(12) United States Patent
Hyde, Jr.

(10) Patent No.: US 7,637,927 B2
(45) Date of Patent: Dec. 29, 2009

(54) TRANSOSSEOUS SPINE CORE APPROACH METHOD IMPLANT AND INSTRUMENTATION

(76) Inventor: Edward R. Hyde, Jr., 102 Benjamin Way, Turlock, CA (US) 95380

( * ) Notice: Subject to any disclaimer, the term of this patent is extended or adjusted under 35 U.S.C. 154(b) by 154 days.

(21) Appl. No.: 11/089,896

(22) Filed: Mar. 25, 2005

(65) Prior Publication Data

US 2007/0118219 A1 May 24, 2007

Related U.S. Application Data

(60) Provisional application No. 60/521,281, filed on Mar. 25, 2004.

(51) Int. Cl.
*A61B 17/88* (2006.01)
(52) U.S. Cl. .................................. 606/279
(58) Field of Classification Search ... 623/17.11–17.16, 623/908; 606/61
See application file for complete search history.

(56) References Cited

U.S. PATENT DOCUMENTS

| | | | |
|---|---|---|---|
| 4,059,115 A * | 11/1977 | Jumashev et al. ............ 606/82 |
| 5,108,404 A * | 4/1992 | Scholten et al. ............ 606/94 |
| 5,827,328 A | 10/1998 | Buttermann |
| 5,888,226 A * | 3/1999 | Rogozinski ............ 623/17.16 |
| 5,893,889 A * | 4/1999 | Harrington ............ 623/17.16 |
| 6,589,281 B2 | 7/2003 | Hyde, Jr. |
| 6,761,723 B2 | 7/2004 | Buttermann et al. |
| 7,114,501 B2 * | 10/2006 | Johnson et al. ............ 128/877 |
| 7,303,565 B2 | 12/2007 | Buttermann et al. |
| 2003/0105527 A1 * | 6/2003 | Bresina ................... 623/17.16 |
| 2003/0199879 A1 * | 10/2003 | Spranza, III ................ 606/79 |
| 2003/0204189 A1 * | 10/2003 | Cragg ......................... 606/61 |
| 2005/0038514 A1 * | 2/2005 | Helm et al. ............ 623/17.12 |
| 2005/0113919 A1 * | 5/2005 | Cragg et al. ............ 623/17.11 |
| 2005/0261684 A1 * | 11/2005 | Shaolian et al. ............. 606/61 |
| 2006/0079898 A1 * | 4/2006 | Ainsworth et al. ........... 606/61 |

\* cited by examiner

*Primary Examiner*—Thomas C Barrett
*Assistant Examiner*—Nicholas Woodall
(74) *Attorney, Agent, or Firm*—Downs Rachlin Martin PLLC

(57) ABSTRACT

The transosseous spinal core approach (TOSCA) represents a novel approach to the interior of the spine or disc space by removing a core from a first bone and performing a procedure, and/or making further enlargements and cuts in the first bone and performing a procedure, and/or making another cut into an adjacent disc space from the first bone hole and performing a procedure and/or continuing by cutting into another second bone and performing a procedure. The process can be further extended into additional spine levels by extending the cutting process. A core can be made at more than one level. The preferred surgical approach is a posterior lateral approach. An anterior surgical approach can be used as well. Any practical surgical approach or any combination of surgical approaches can be utilized to gain access to the first bone. Once the surgical soft tissue access to the first bone is completed TOSCA can be used to gain access to the interior of a vertebral body or disc space. After the procedure is completed in a vertebral body or disc space, usually at least a portion of the bone core is replaced to fill in the core hole.

36 Claims, 32 Drawing Sheets

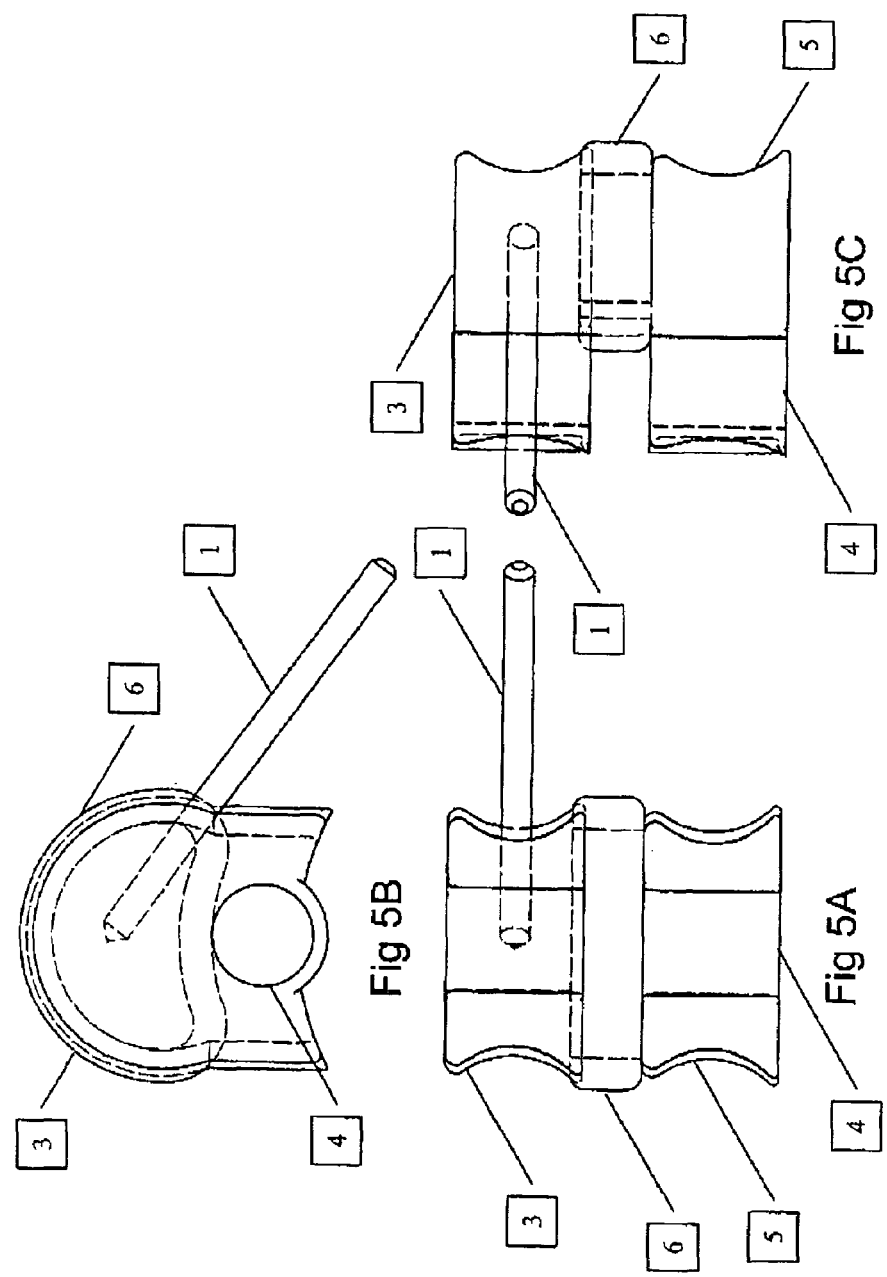

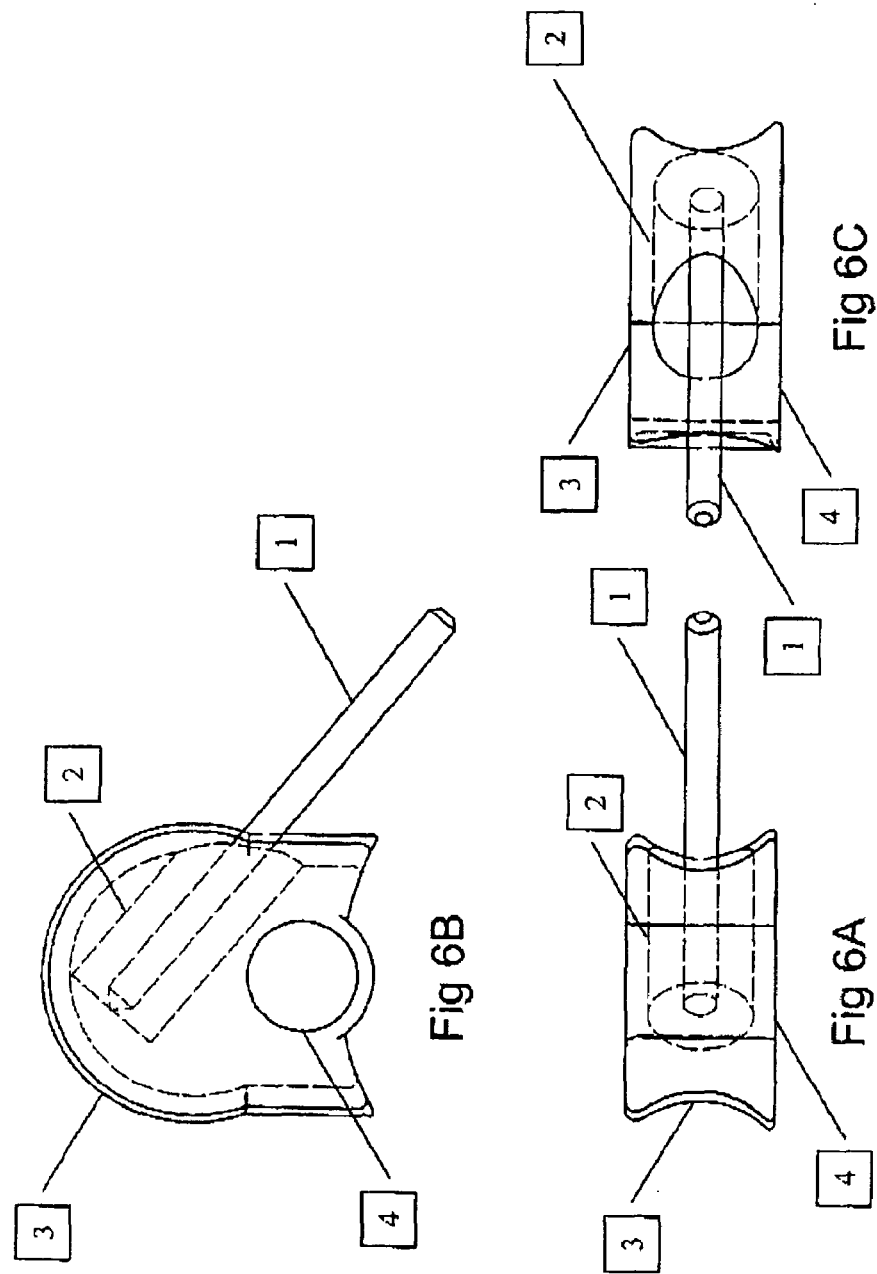

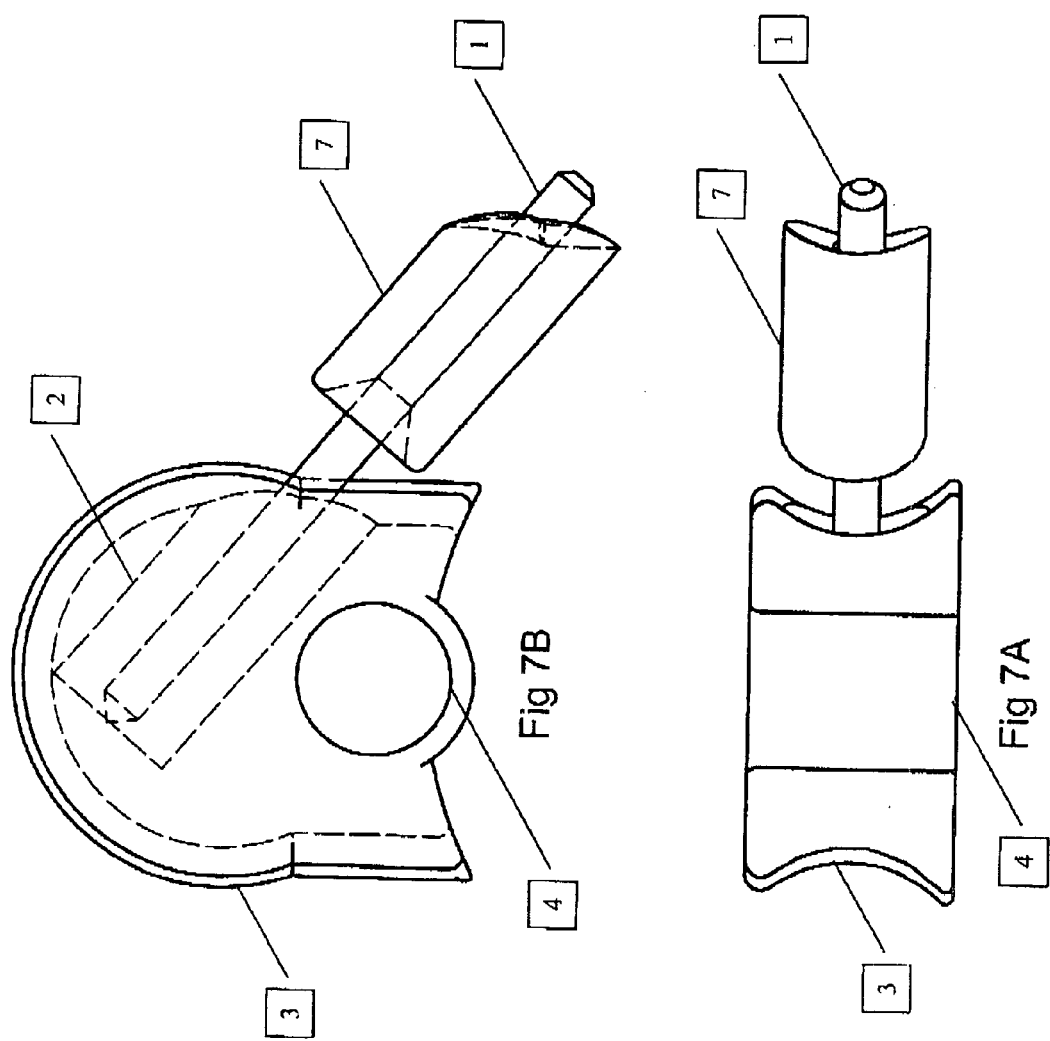

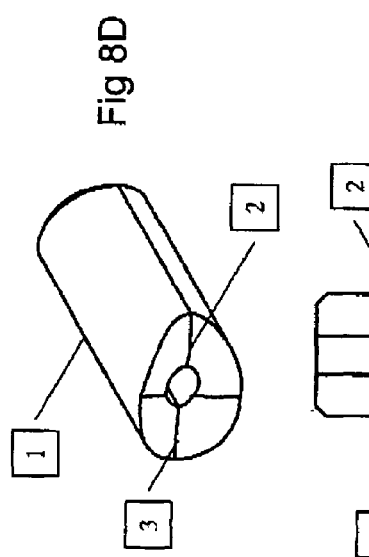
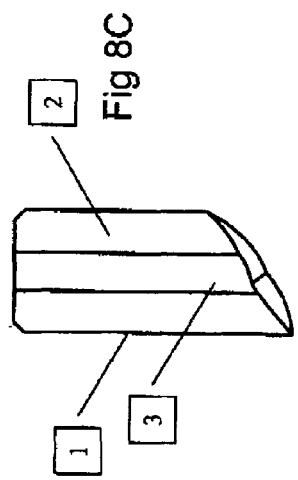
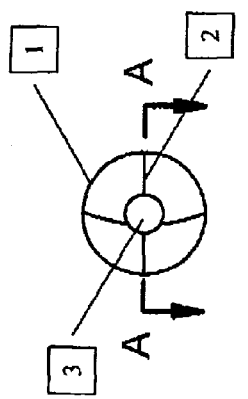
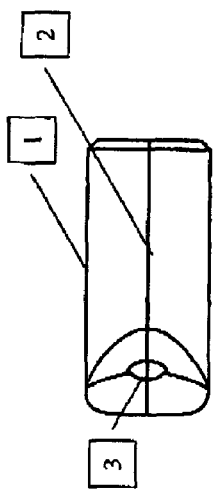
Fig 8D
Fig 8C
Fig 8B
Fig 8A
SECTION A-A

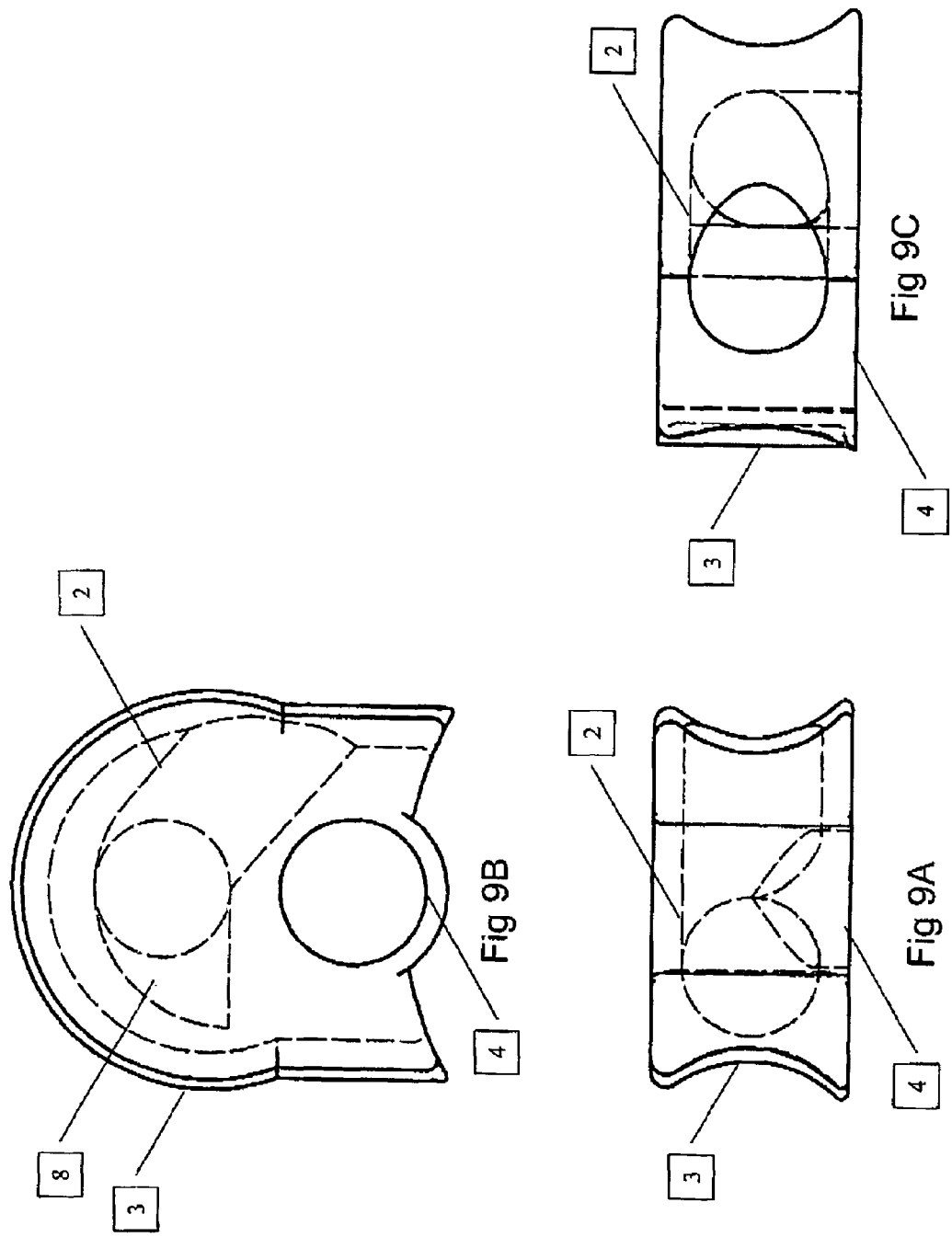

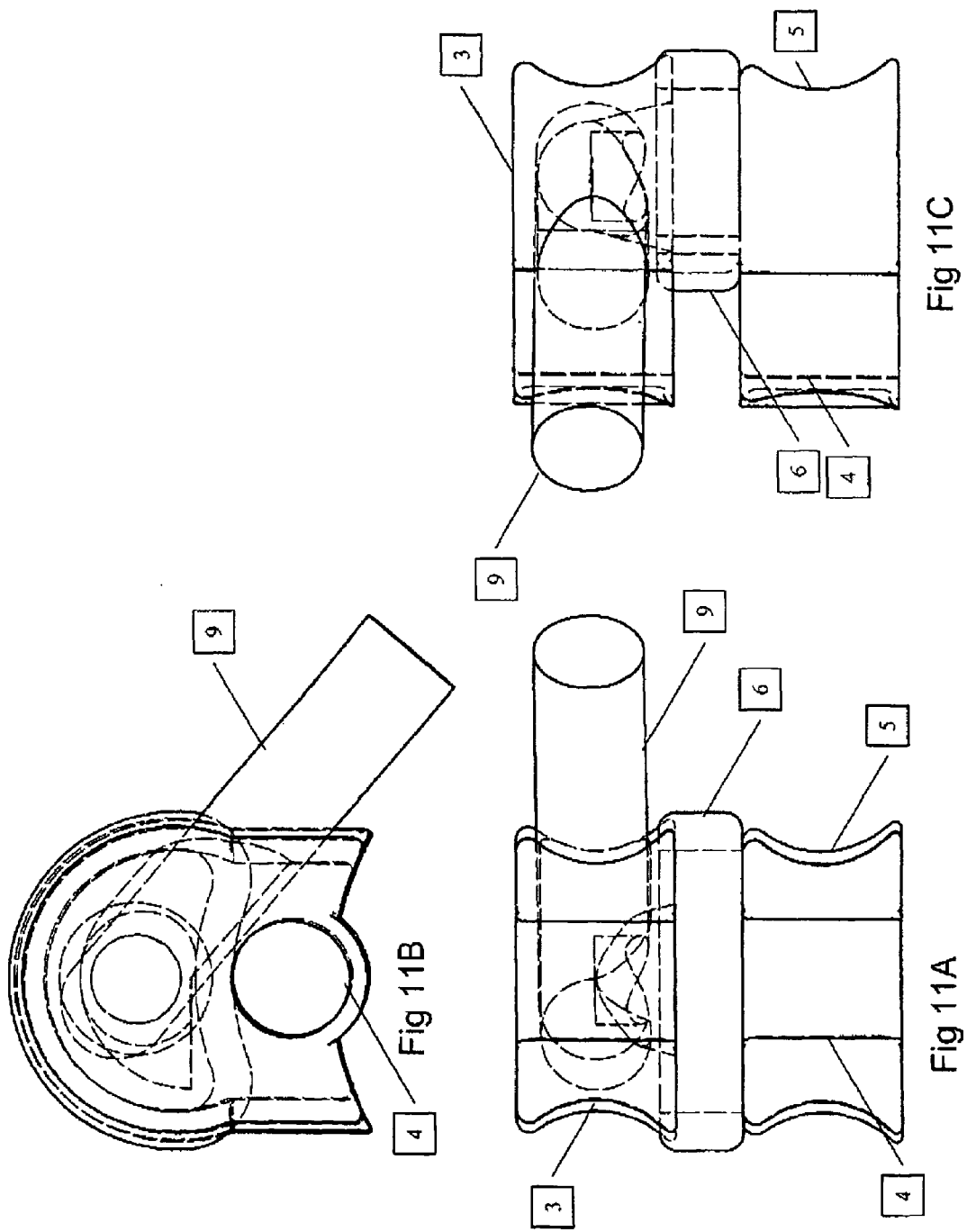

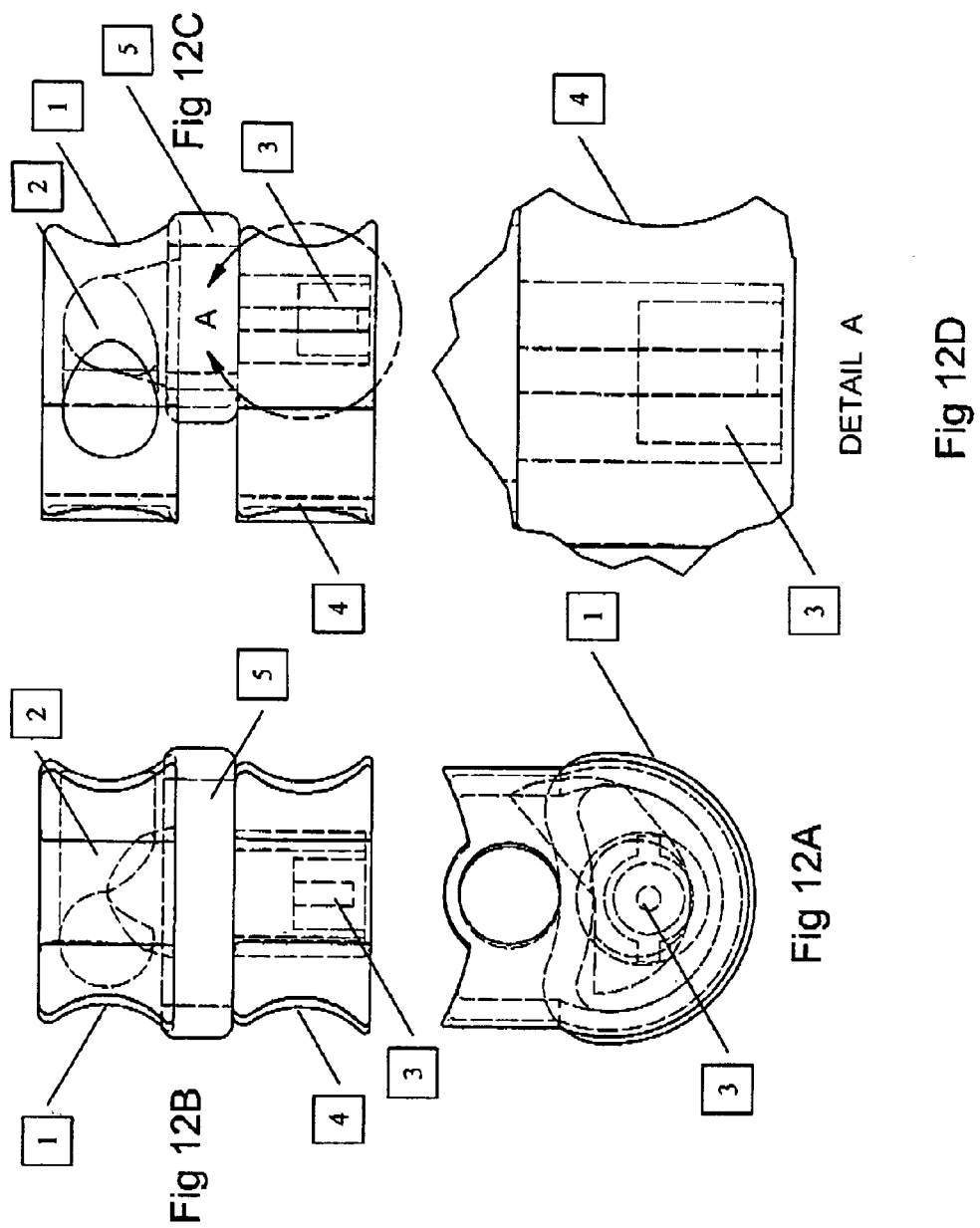

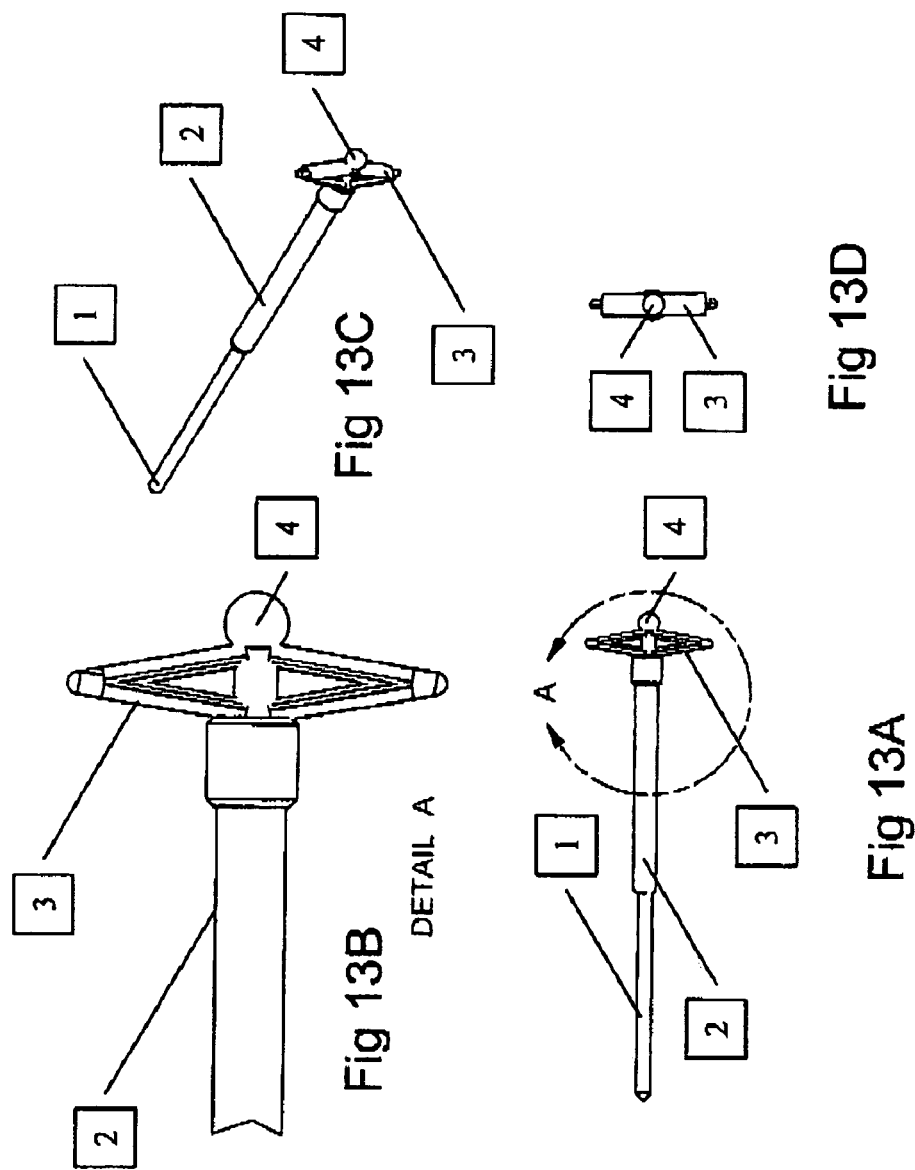

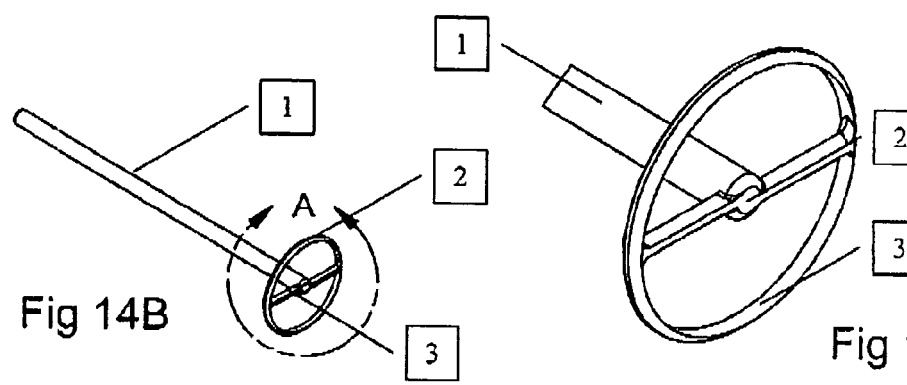
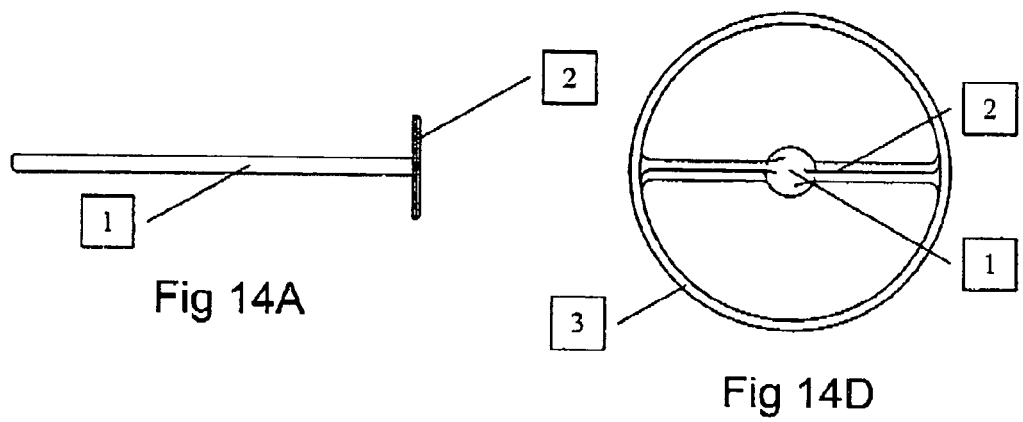
Fig 14B
Fig 14C
Fig 14A
Fig 14D

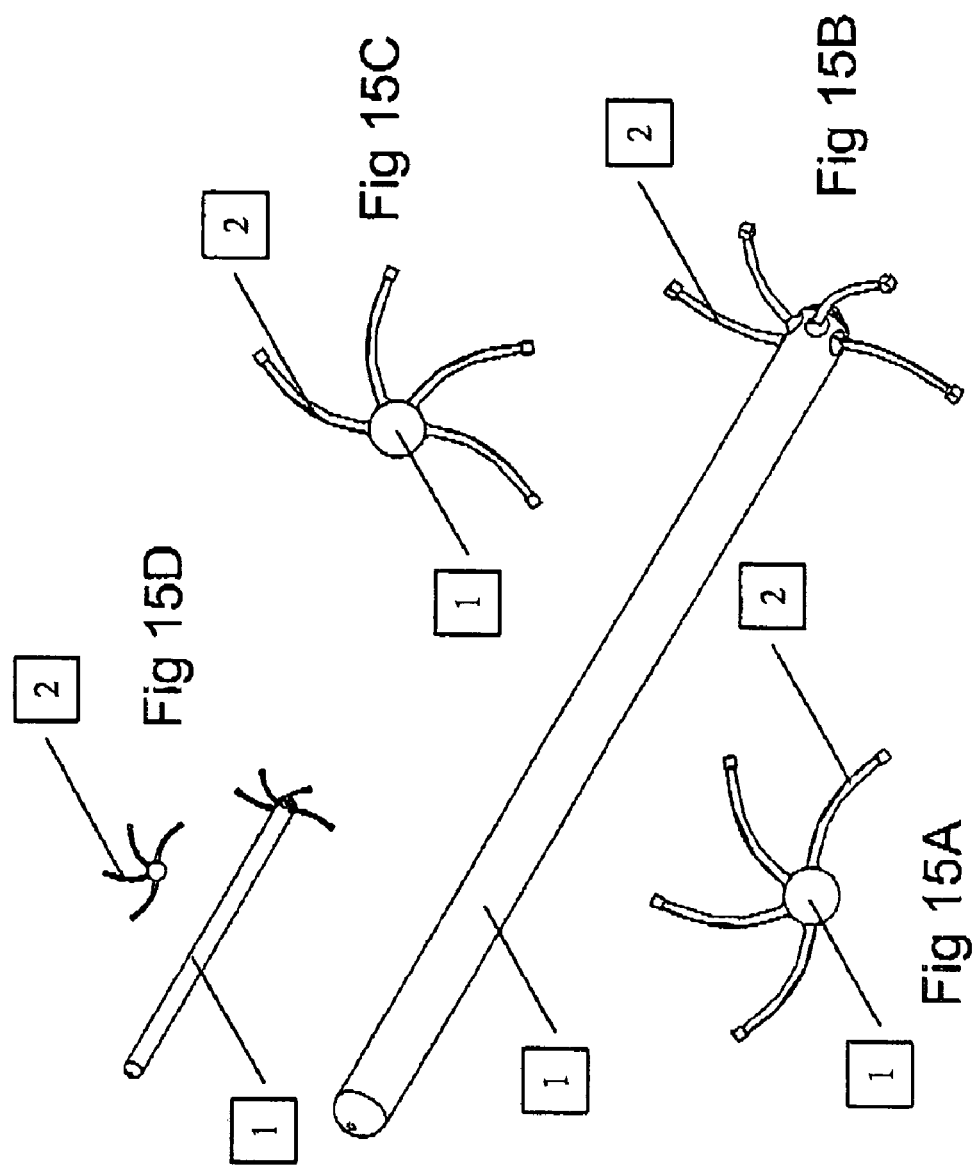

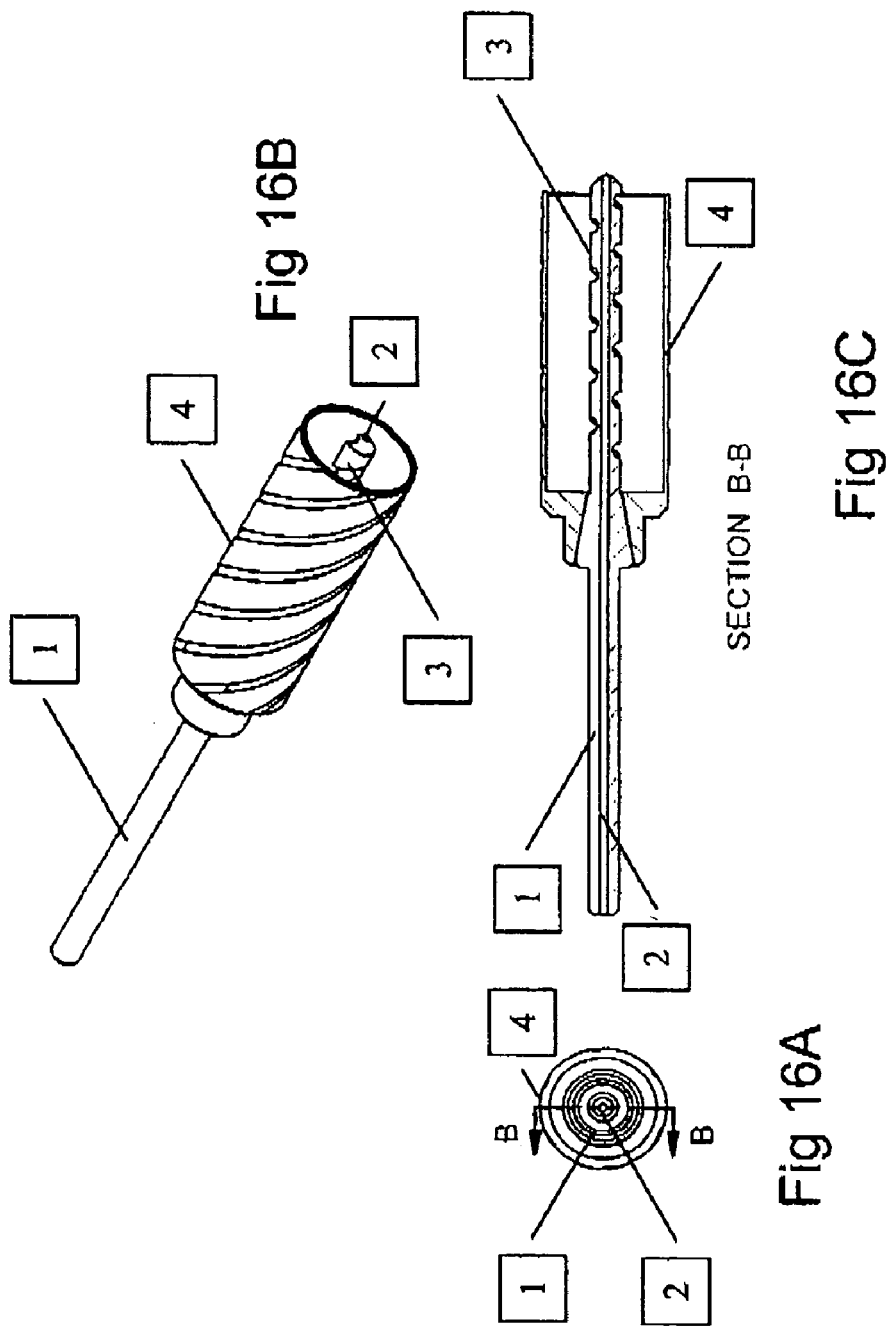

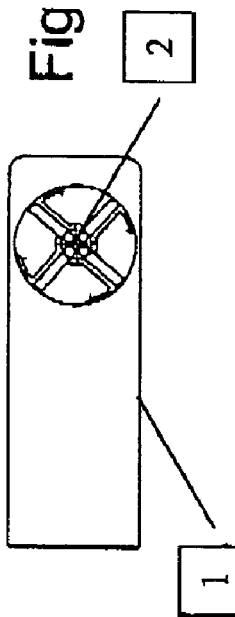
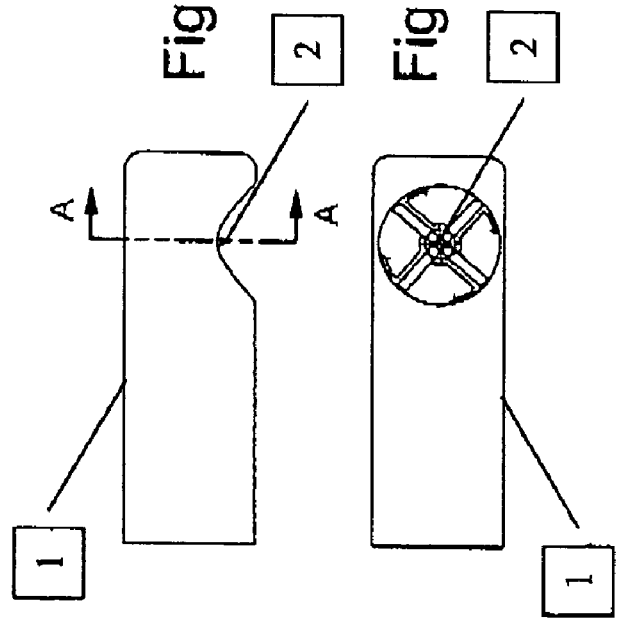
Fig 17A
Fig 17B
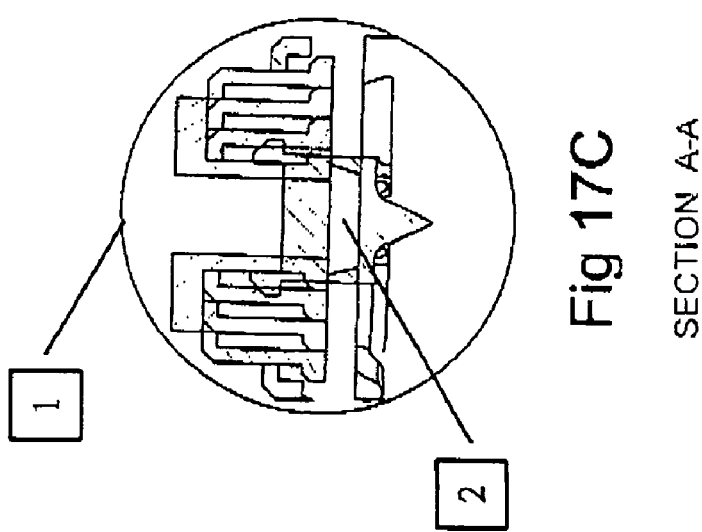
Fig 17C
SECTION A-A

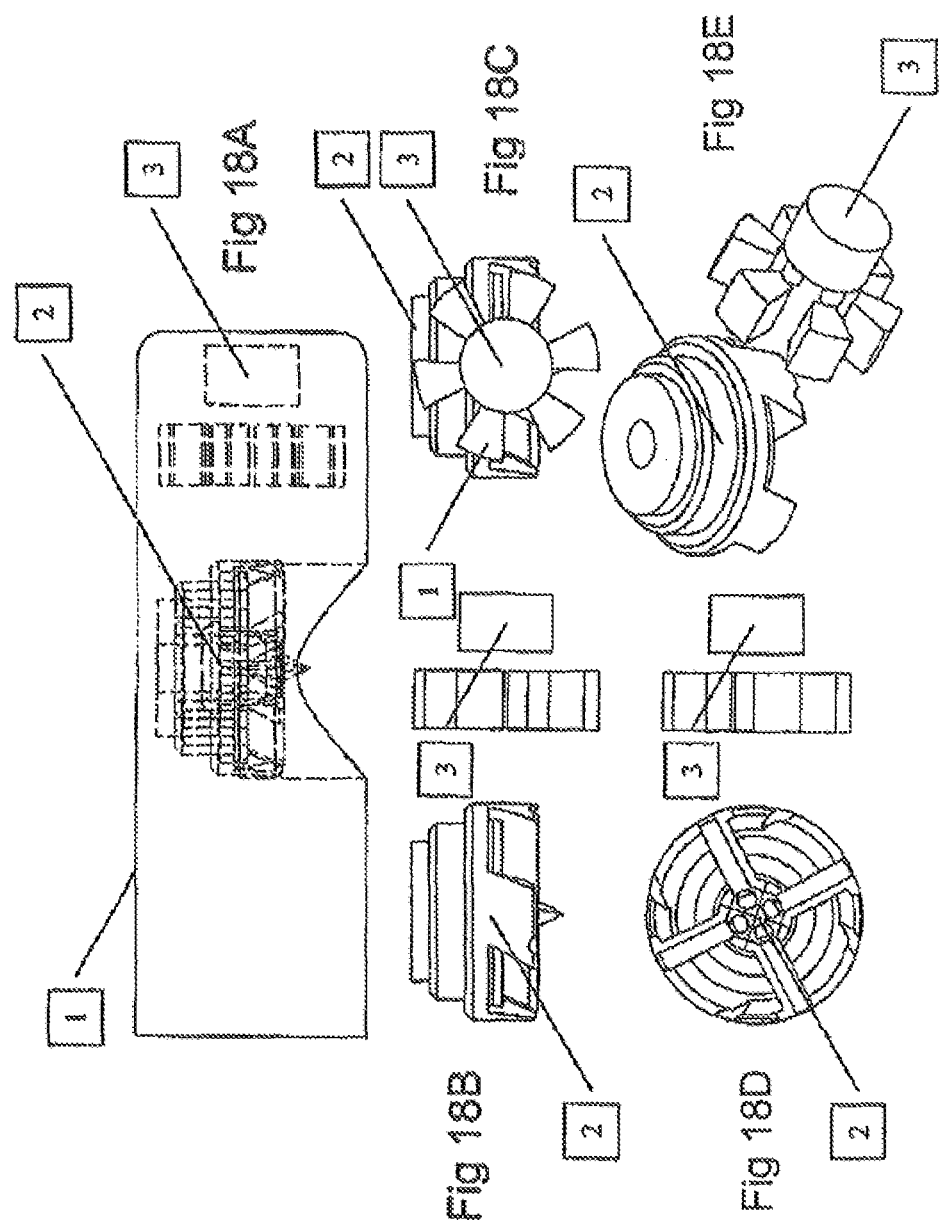

SECTION A-A

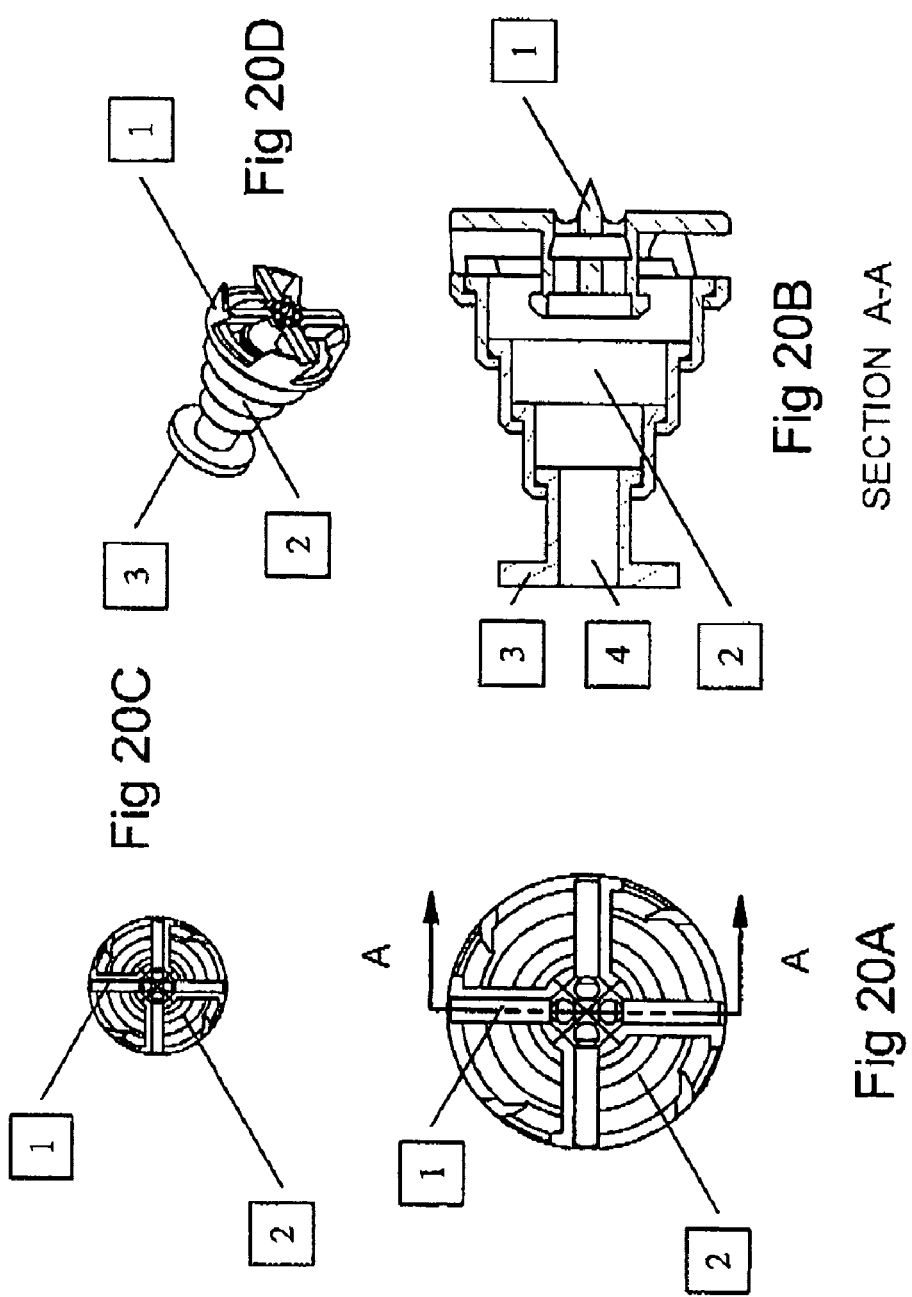

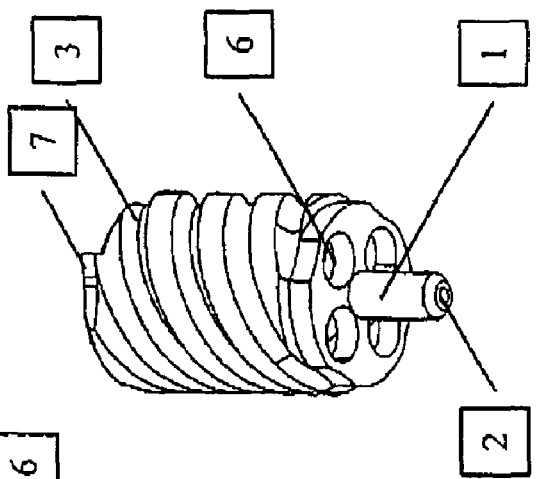
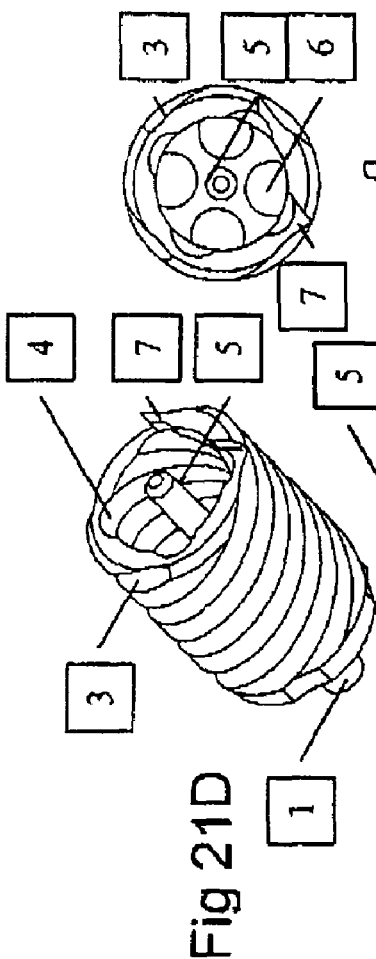
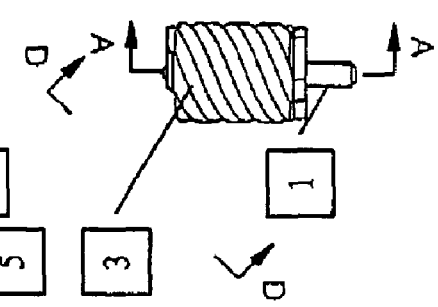
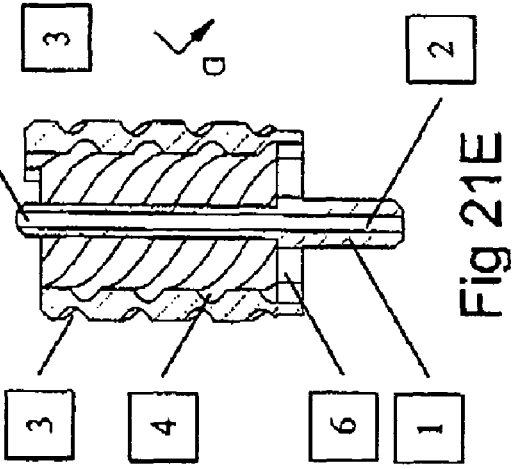
Fig 21C
Fig 21B
Fig 21A
Fig 21D
Fig 21E

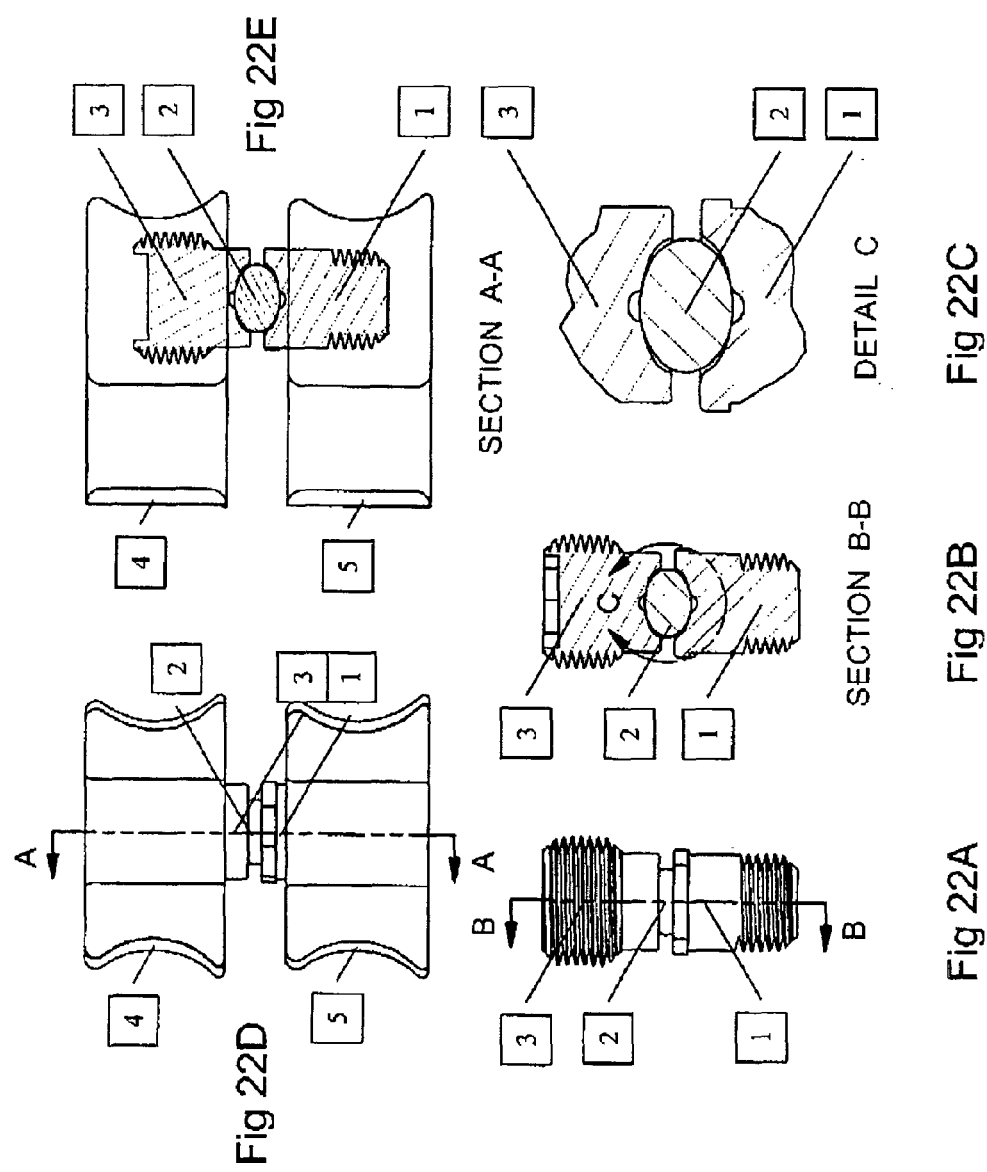

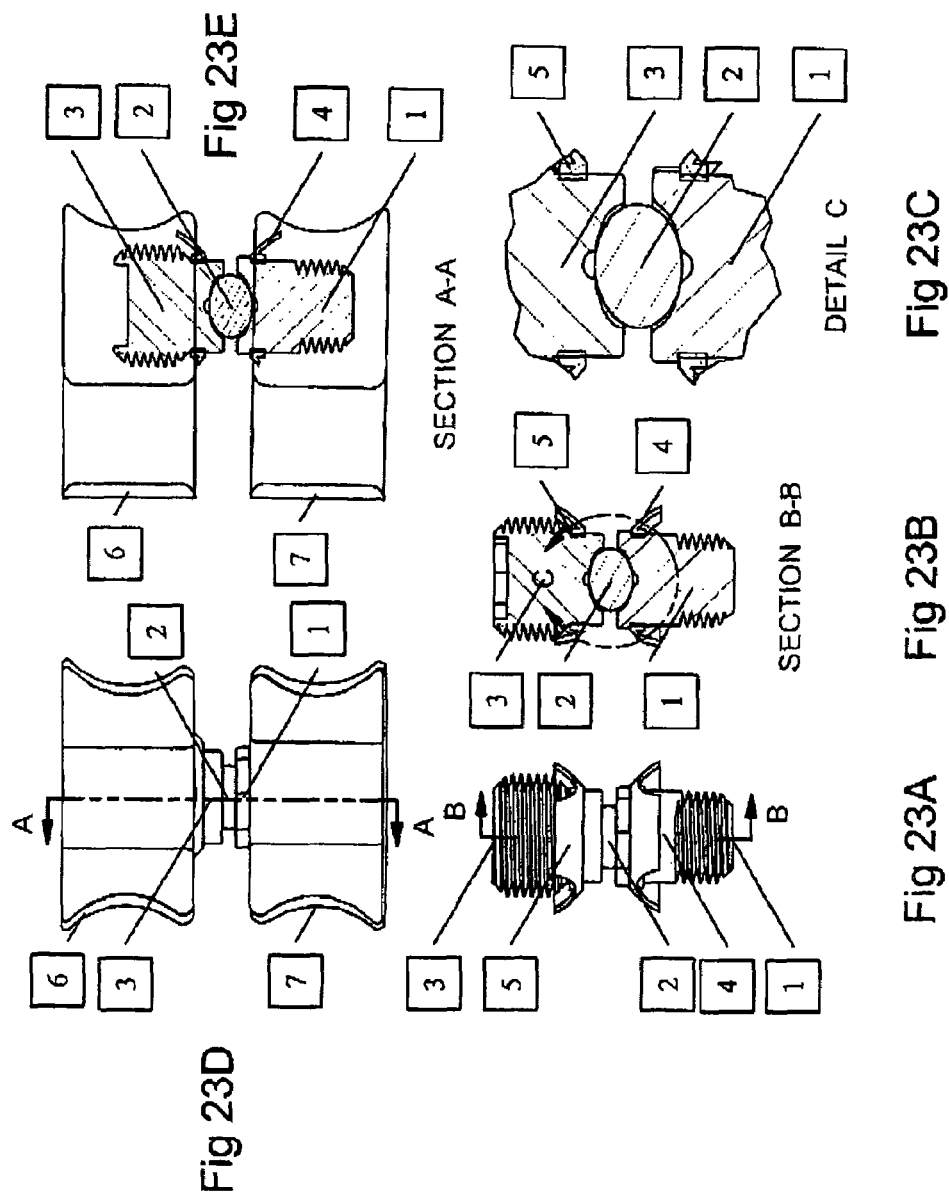

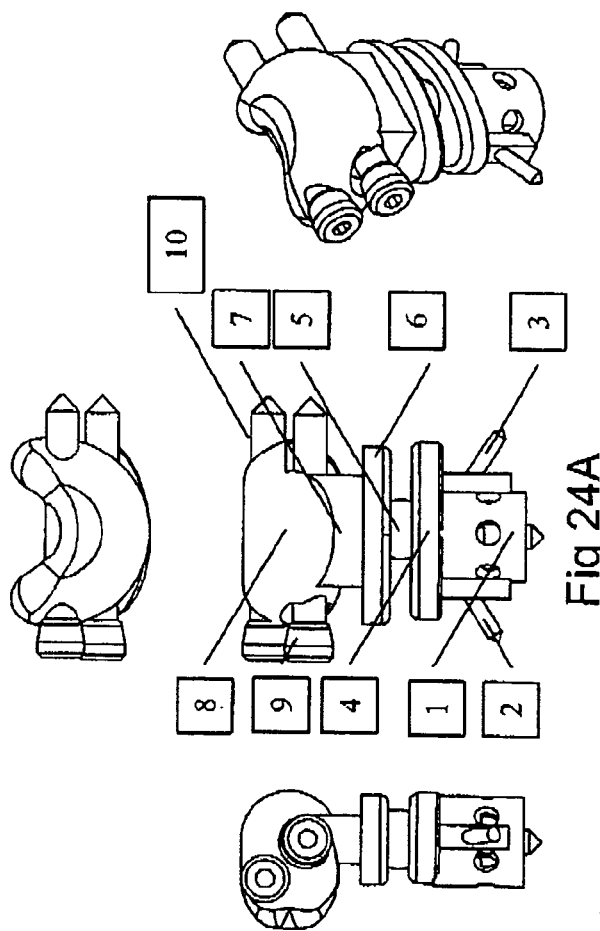

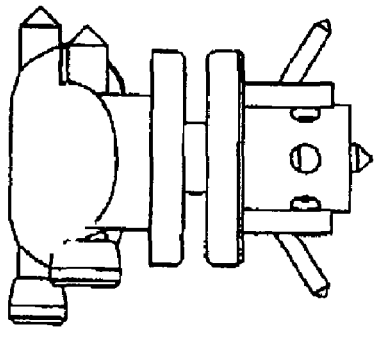
Fig 25E
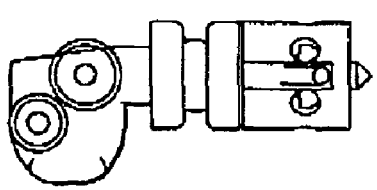
Fig 25B
Fig 25C
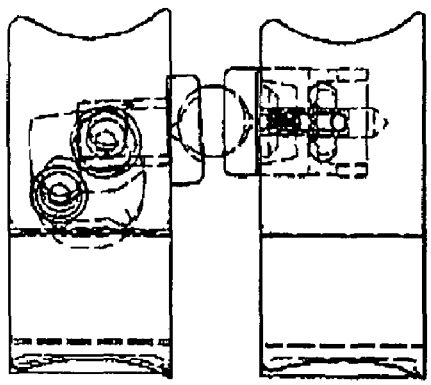
Fig 25D
Fig 25A
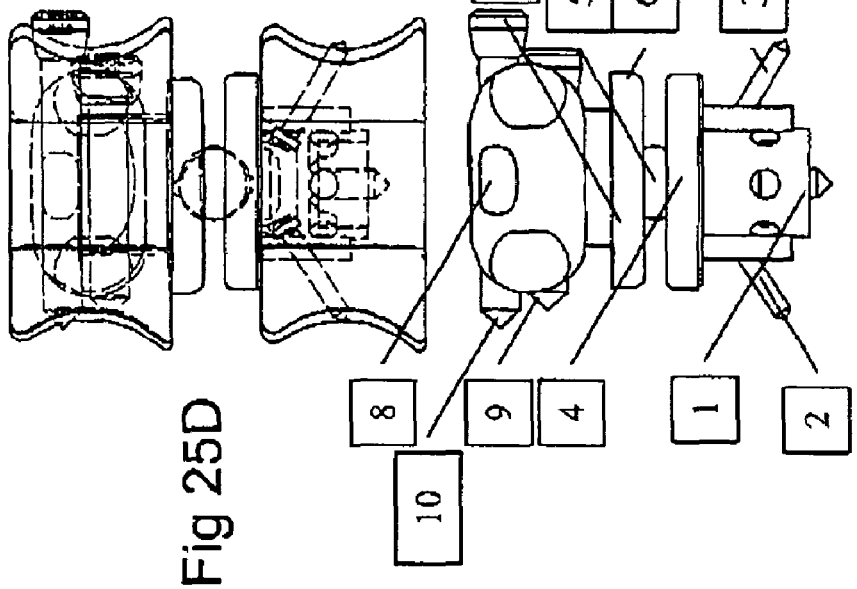

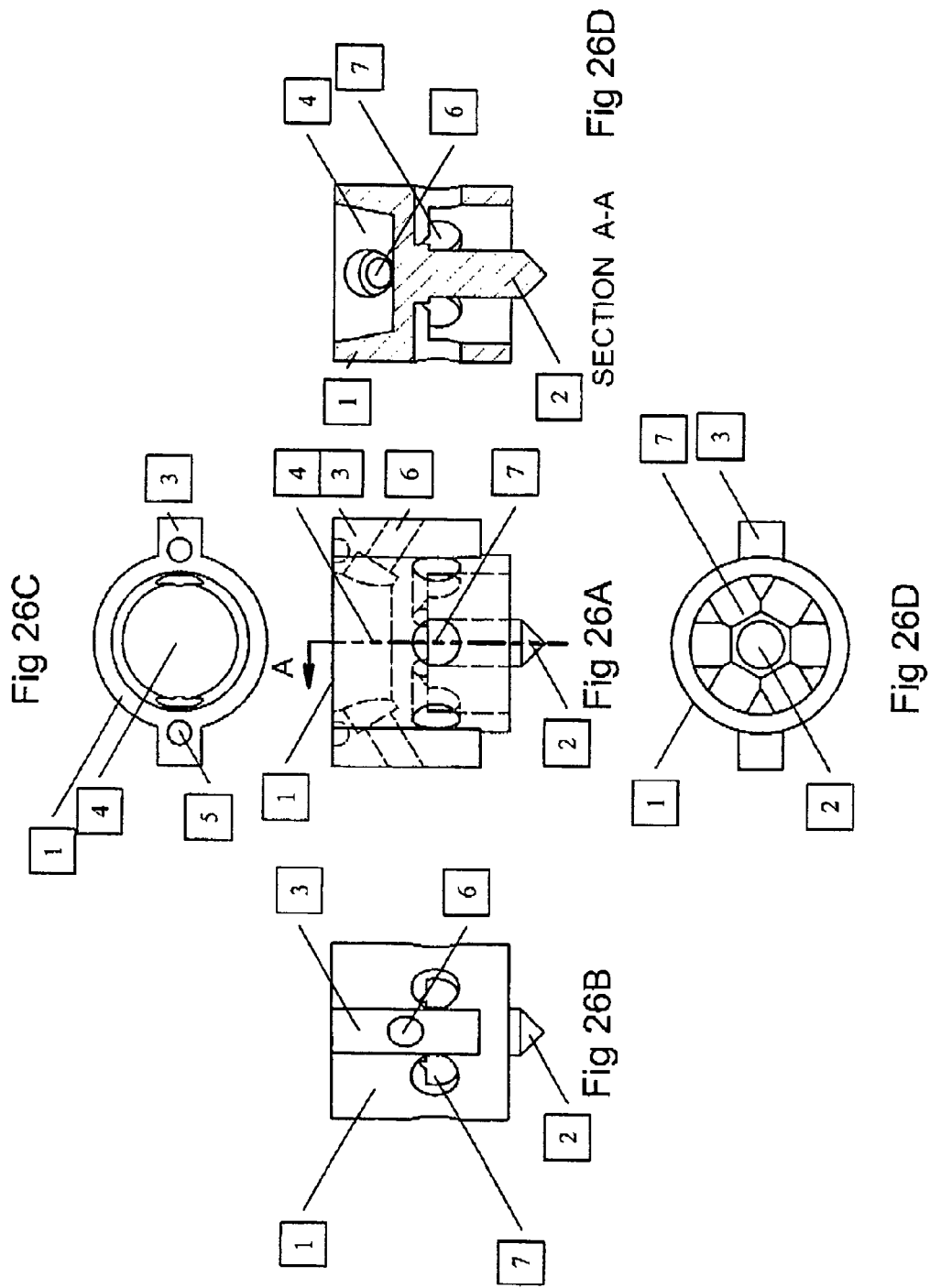

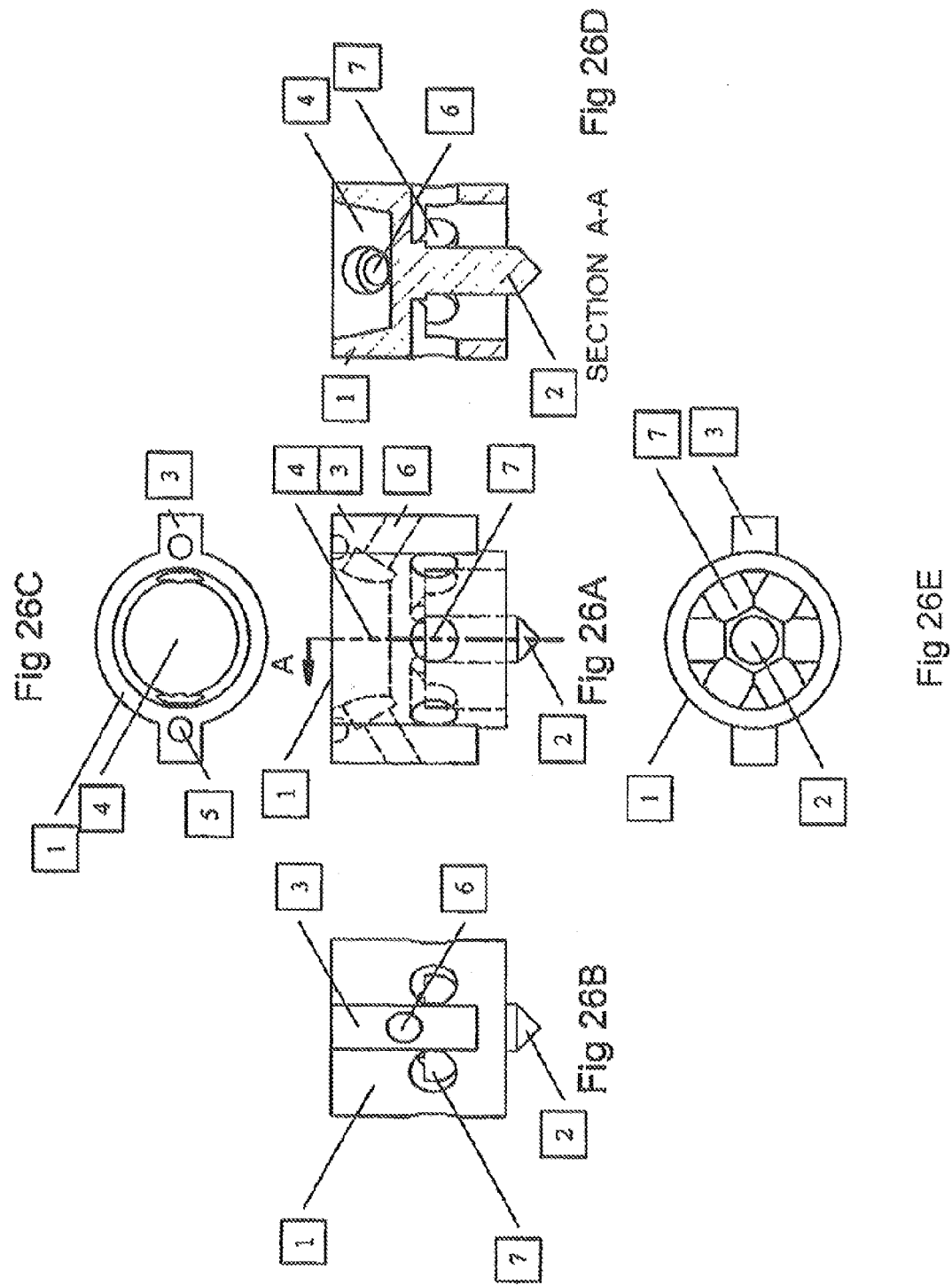

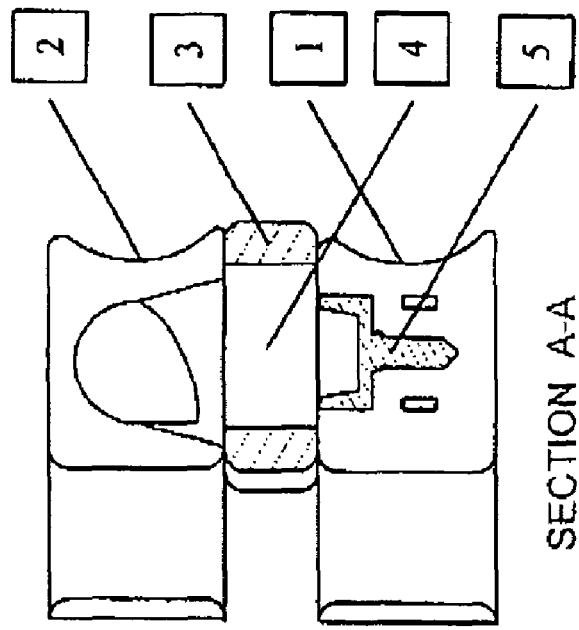
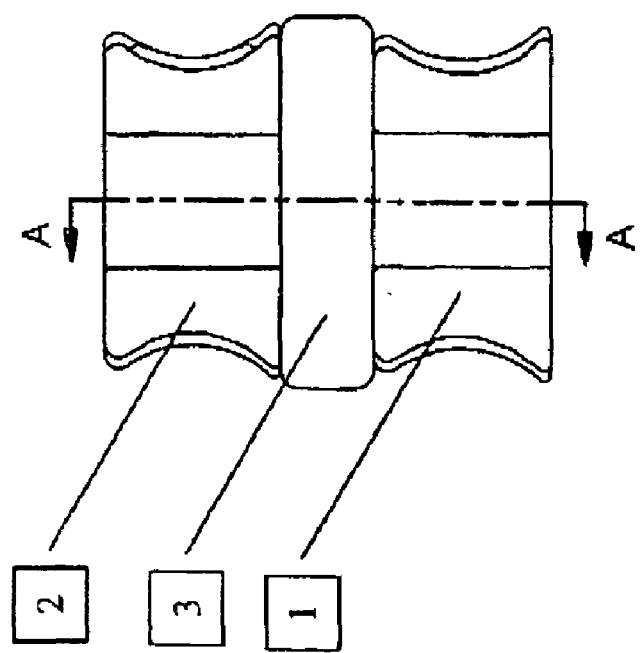
Fig 27B
Fig 27A

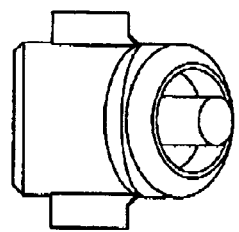
Fig 28D
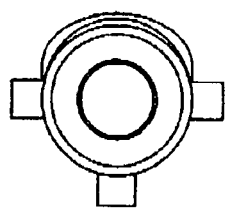
Fig 28C
Fig 28A
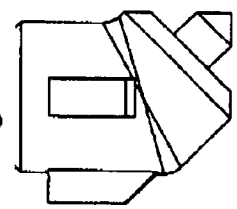
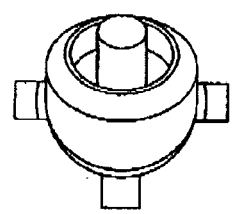
Fig 28E
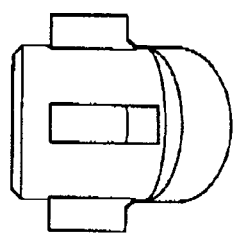
Fig 28B

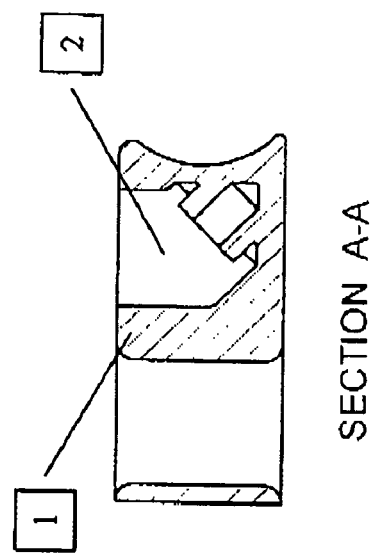
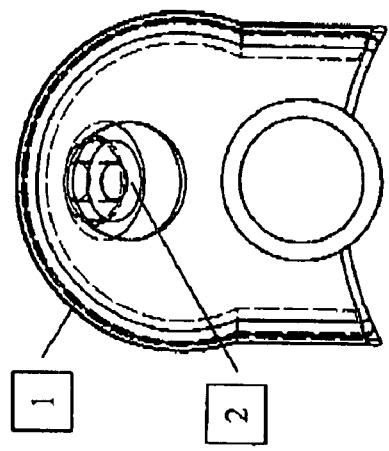
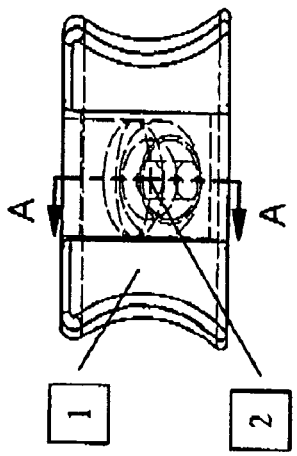

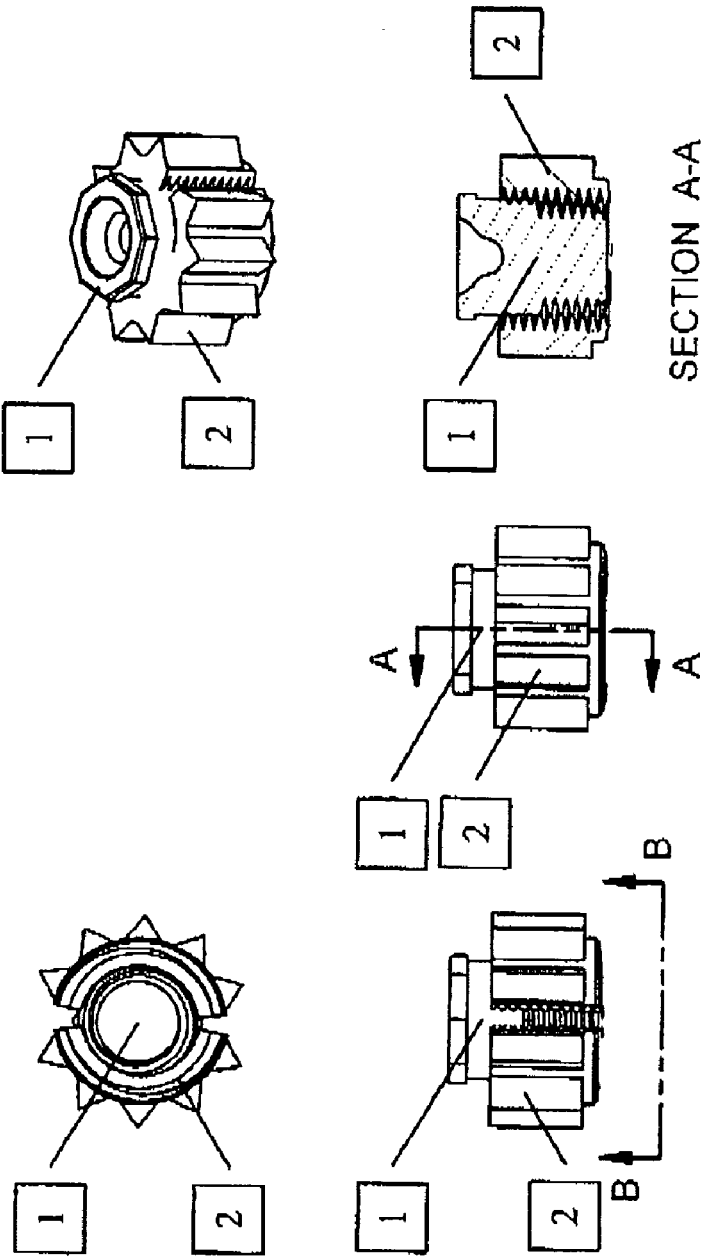

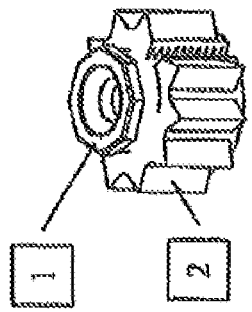
Fig 30B
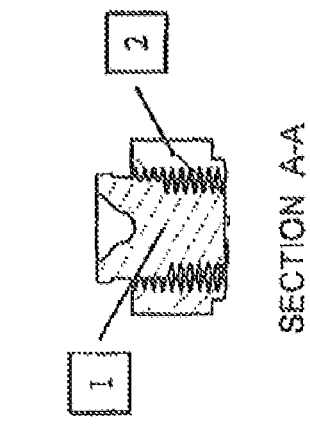
SECTION A-A
Fig 30E
Fig 30D
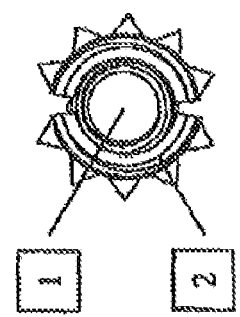
Fig 30A
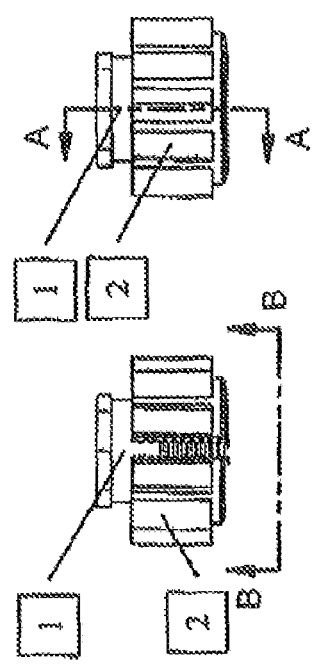
Fig 30C

TRANSOSSEOUS SPINE CORE APPROACH METHOD IMPLANT AND INSTRUMENTATION

This application claims benefit of provisional application No. 60/521,281, filed Mar. 25, 2004.

BACKGROUND OF THE INVENTION

The present invention provides a method, instrumentation and implants to treat pathology of the spine, typically degenerative disc disease or degenerative joint disease. The methods and instrumentation can be used to treat the spine for other pathologies such as fractures, tumor, etc., with or without implants. This invention is related to the disclosure in U.S. Pat. No. 6,589,281, which is fully incorporated by reference herein.

Degenerative spine pathology has been recently treated with some method of fusion of parts of the spine to stop motion and reduce pain. There are many known methods of spine fusion. Pedicle screws have been favored by some surgeons to increase the success of the fusion surgery which relies on the formation of a success of the fusion surgery which relies on the formation of a solid bone mass from the bone of the vertebral bodies and bone graft. Spinal cages have also had some success in improving fusion rates.

Fusion sacrifices motion for pain. Stresses that are usually accommodated at the fused level are transmitted or moved to adjacent vertebrae and are felt to accelerate degenerative joint disease at levels above and below the fusion site.

Spinal disc replacements have been recently developed, using UHMWPE and cobalt-chrome (CoCr). Other material combinations are also used. Currently spinal disc replacements are investigational devices in the U.S. There are disc designs for cervical and lumbar pathology. The different regions of the spine require different engineering and surgical considerations. This has led to multiple spine disc products that vary in forms, applications and materials. The surgical approach for the cervical and lumbar spine disc replacements has been typically via an anterior approach that can be complicated and hazardous. The anterior approach removes additional portions of the disc annulus fibrosus to provide exposure to insert the artificial disc, compromising the structural integrity of the spine disc mechanics. Some approaches for spine disc replacement require the assistance of a general surgeon to help with the exposure.

SUMMARY OF THE INVENTION

The posterior lateral approach is a preferred method for using the transosseous spine core approach (TOSCA) of the invention and will be described in detail. The basic technique elements are followed once the vertebra is exposed. There are regional variations in anatomy at and within various levels of the spine requiring associated modifications of methods, instruments and implants. TOSCA can be used to access any vertebra from any direction that a surgeon feels gives him a more desirable access. The anterior approach or any other approach can be used to take the core if desired.

A minimally invasive posterior-lateral approach for the spine will be described in detail as a preferred example, which is a variant of the well described posterior, lateral or transpsoas approaches. Different steps for the approaches might be needed for cervical, thoracic or other lumber levels than L4-L5.

Surgical Approach
Example: Posterior-Lateral Access to Lumbar L4-L5

The patient is typically placed in the right lateral decubitus position. This will vary depending on the anatomical area and surgeon preferences.

An approach to treat L4-5 disc pathology will be used to illustrate one of the TOSCA approaches.

A small incision is made lateral to the midline and to the right, centered over the pedicle or transverse process of the L4 vertebral body. The incision position and depth depends on the patient size, habitus and surgeon preference. Soft tissue dissection is carried down to the junction of the transverse process and the L4 vertebra. The transverse process is divided from the vertebra body at its base and reflected out of the field. Further dissection is carried out next to the bone or subperiosteal to expose the lateral surface of the L-4 vertebral body. Hemostasis is performed in the usual fashion.

A guide pin is inserted into mid body of L4 guided by an instrument that aids placement of the guide pin at the preferred angle to the sagittal plane. The guide pin is placed at an angle of substantially 50 degrees (40-75 degrees) from a point in the center of the L4 body directly above and centered on the footprint of the nucleus pulposa below (L4-5) and also on a line centered in the L4 body on a line through the center of the L4 body and spinous process in the sagittal plane. This angle is for the specific posterior lateral approach described. This angle can be varied as necessary. A first vertebral body can be entered at any angle preferred by the surgeon. The guide pin is simultaneously placed parallel to the disc plane (L4-5) and centered in the L-4 body. The guide pin is advanced and the position is checked using x-rays, ultrasound, computer navigation systems and/or any combination and/or any other available methods. Once the pin is in place and centered, a bone core substantially 0.8". in diameter is cut from the body of L4 using the TOSCA core cutting instrument. The diameter of the core is based on the largest practical diameter that will allow exposure without compromising the endplates of the vertebra. It can be smaller or larger than 0.8" in diameter. This size restriction is not an absolute and the endplates can be cut if so desired. The bone core is then removed using a specialized method and core transecting instrument. The cavity can be expanded using curettes, burrs or any other cutting instruments and the bone is saved for possible later implantation. More than one vertebra can be accessed via a core cut during a procedure. Two or more adjacent levels can be approached i.e. L4 & L5 or levels spaced apart (i.e. L2 & L5).

The axial reamer is then introduced through the bone core hole and the position is verified using on board ultrasound sensors (if so equipped), computed navigation systems, etc., second bone cut is made substantially perpendicular to the inferior vertebral endplate of L4 centered substantially over the L4-5 nucleus pulposa footprint. The cut is made through the L4 endplate and into the space of the L4-5 nucleus pulposa. Some of the annulus fibrosus, nucleus pulposa or disc remnants may also be removed at this time. The procedure can be terminated at this point after the pathology has been treated and the bone and bone core replaced.

Next the post cutter is introduced through the bone core hole and into the L4-5 disc space. The post cutter makes the cut through the upper surface of L5 and into the cancellous bone of L5. The depth is variable depending on the implant being used. This cut is continued until the proper depth for the implant has been reached. Some L5 implant embodiments rest on the inner surface of the inferior endplate, so they require the cut to be made through all of the cancellous bone of L5.

This axial cut can be extended through to the endplate of L5 and into the L5-S1 disc space or further. It can be extended through as many vertebral segments as desired. Likewise axial cuts can be made into vertebra above L4 proceeding in the cephalad direction. The core can be taken at another lumbar level such as L3, etc., or it can be a cervical or thoracic vertebral body. The direction of implantation can be reversed (i.e. Taking the bone core from L5 to treat L4-5 disc pathology) from the described cephalad to caudad direction. The operative field is prepped for bone grafting or cement and further prepared for the implants.

The L5 implant is introduced into L4 via the aperture made by the bone core removal, centered and then implanted into the L5 vertebral body. The position is verified. The implant can be cemented or press fit with or without bone graft. Accessory fixation such as screws, pins and the like can be used.

The interposed bearing surface articular element (AE) is placed on/into the L4 or L5 component. These can be rigid, plastic, elastic, viscoelastic, etc. The articular bearing surface (AS) can be part of another component (i.e. the L4 component or the L5 component). The AE can be any substantially curvilinear shape. It can be an elongation of a component (i.e. L4) that articulates with a depression in another component (i.e. L5). Typically it is a separate part substantially in the shape of an ellipsoid, toroid, etc. It can be one or more than one part. For example, it can be a ellipsoid and a toroid in combination such as a toroid surrounding an ellipsoid or many ellipsoid or other shape pieces arranged in a toroidel pattern. There can be more than one interposed AE. The multiple AEs can be made of different materials and have different shapes. The interface can in another embodiment be generated by only magnetic fields or by magnetic fields in combination with AEs or other mechanical surfaces. The magnetic material can be in/on the interface, in/on the flanges, in/on the fixation or at any place in the components. They can also be placed separately from the components in the bone, or adjacent to the bone. The interface can likewise include additional flanges or other stabilizing structures.

The L4 component is then inserted into L4. L4 and L5 can be modular, for example a fixation module, an articulation module and/or a stabilization module. Once it is in position it is advanced until it engages the interposed AE or component. Appropriate pressure is applied with a torque driver or other apparatus to ensure proper pressure between the components. The bone core is replaced and can be additionally secured if necessary with a screw, staple, pin or the like. Flexion is checked and verified. Standard closure is accomplished.

This embodiment is a simple preferred embodiment to simplify the procedure and reduce surgical time. Additional components can be added to effect better fixation, stability and the like. Flanges that contact or rest on the upper surface of L5 in the L4-5 disc space and contact or rest on the inferior surface of L4 in the L4-5 disc space can be added.

Screws, pins rods and the like can be used to add additional fixation. Some of specific implant embodiments will be discussed in detail.

Surgeons can implant the spine implants through optional approaches other than the posterior approach such as the anterior approach currently used in spinal disc replacement. Surgeons can treat other pathologies using TOSCA from other approaches or combinations of approaches such as a combination of right and left posterior, posterior and anterior or any combination of any approaches. These and other objects, advantages and features of the invention will be apparent from the following description of a preferred embodiments, considered along with the accompanying drawings.

DESCRIPTION OF THE DRAWINGS

FIG. 5, 3 views: guide pin insertion into L4.
FIG. 6, 3 views: transosseous core cut.
FIG. 7, 2 views: removal of core.
FIG. 8, 4 views: core—transected.
FIG. 9, 3 views: expansion of aperture.
FIG. 11, 3 views: axial cutter placement in L4.
FIG. 12, 4 views: axial cut through L4 & into L4-5 disc space.
FIG. 13, 4 views: core transector (embodiment 1).
FIG. 14, 4 views: core transector (embodiment 2).
FIG. 15, 4 views: core transector (embodiment 3)
FIG. 16, 3 views: core device (embodiment 1)
FIG. 17, 3 views: axial cutter (embodiment 1)
FIG. 18, 5 views: axial cutter (embodiment 2) with detail.
FIG. 20, 4 views: axial cutter cutting mechanism (embodiment 1) open.
FIG. 21, 5 views: crown and post cutter (embodiment 1) with detail.
FIG. 22, 5 views: spine prosthesis (embodiment 1) detail and inserted.
FIG. 23, 5 views: spine prosthesis (embodiment 2) detail and inserted.
FIG. 24, 5 views: spine prosthesis (embodiment 14) detail.
FIG. 25, 5 views: spine prosthesis (embodiment 14) detail and inserted.
FIG. 26, 5 views: crown and post fixation (embodiment 1) detail and inserted.
FIG. 27, 2 views: crown and post fixation (embodiment 1) inserted.
FIG. 28, 5 views: crown and post fixation (embodiment 2) detail.
FIG. 29, 3 views: crown and post fixation (embodiment 2) inserted.
FIG. 30, 5 views: spine prosthesis (embodiment 1) fixation enhancement.

DESCRIPTION OF PREFERRED EMBODIMENTS

The preferred TOSCA method and surgical approach will be described in detail with selected embodiments of methods, instruments and implants. TOSCA is very adaptable to variations in surgical approach, location of entry into a bone, level of entry, procedures, instruments, and implants. Multiple levels can be addressed. A core can be made in more than one bone to facilitate a procedure.

Combined surgical approaches can be used (anterior and posterior, right-left, posterior lateral, etc.). Cutting methods and instruments can be adapted for specific clinical problems. The types of procedures that can utilize TOSCA are limited only by a surgeon's imagination. Implants are substantially designed for each application with variations for vertebra in the cervical, thoracic and lumbar regions. There are also substantially different implant and instrumentation designs for different vertebra in the same region (i.e. C3 vs. C6).

Figures 1A, 1B:
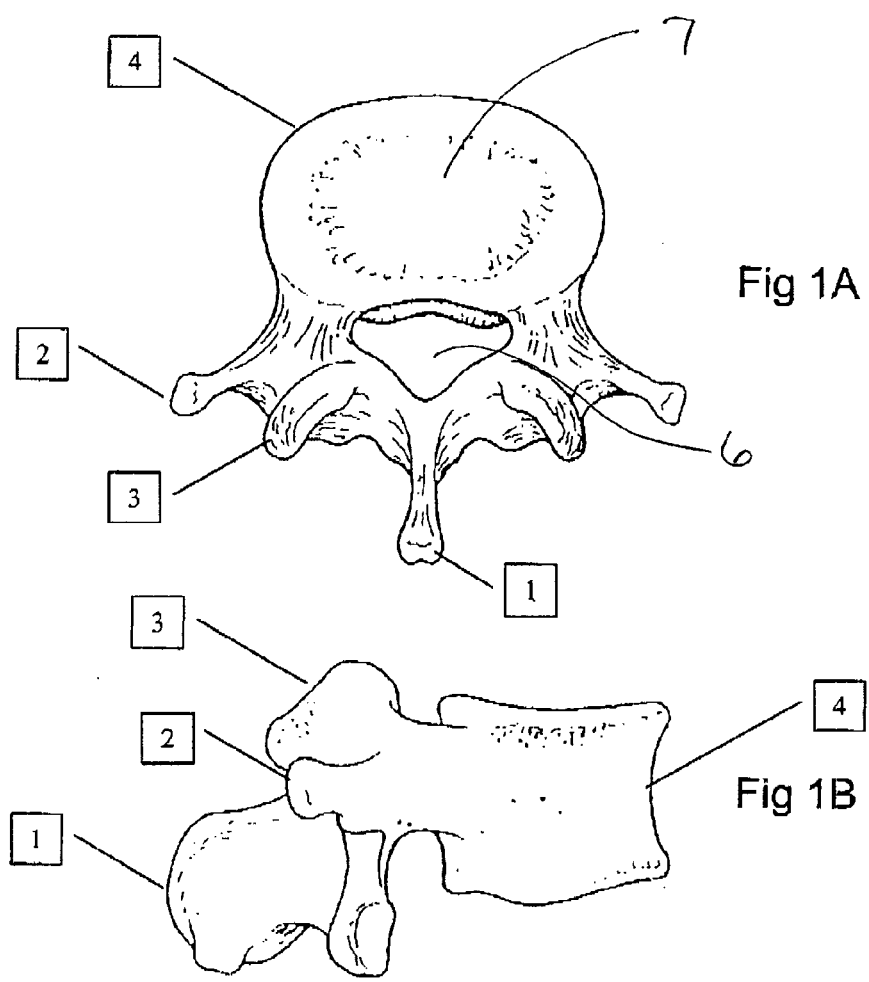
FIG. 1, lumbar vertebra: A—axial view, B—lateral view.

FIGS. 1A and 1B show the axial (A) and lateral (B) anatomy of a vertebra, specifically a lumbar vertebra is shown. TOSCA can be performed at any level of the spine. In FIGS. 1A-4 the spinous process is shown at 1, the transverse process at 2, the superior articular process at 3, the vertebral body at 4, the disc at 5, the vertebral foramen at 6, and the endplate of the vertebra at 7.

Figure 2A:
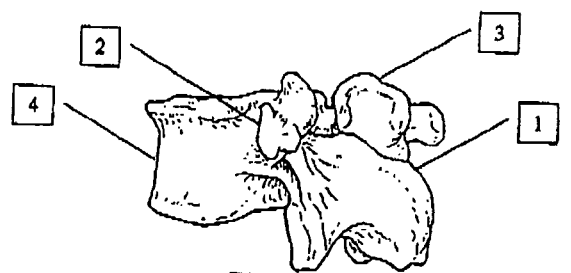
FIG. 2, lumbar vertebra: A—rotated clockwise, B—rotated counterclockwise.
Figure 2B:
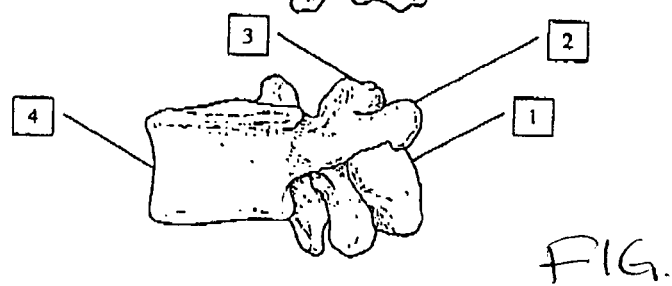

FIGS. 2A and 2B show two related partial rotations between a lateral and a posterior view.

Figure 3:
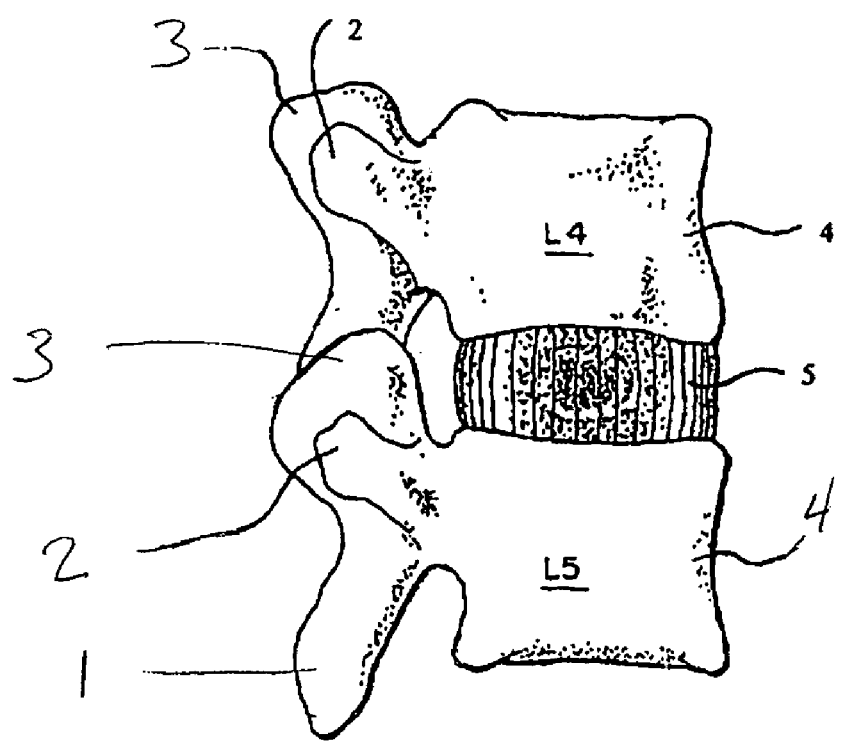
FIG. 3, L4-L5 lumbar vertebrae: lateral view.

FIG. 3 shows two adjacent vertebrae, L4 and L5. This is a very common level for spine pathology and this level will be used for general description of TOSCA.

Figure 4:
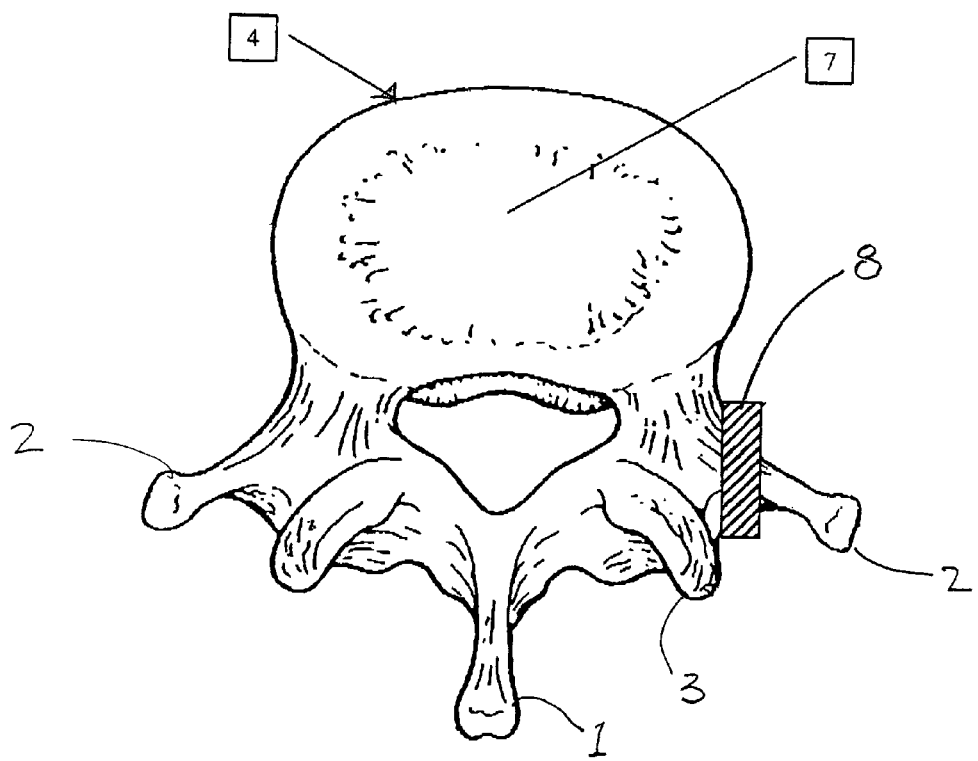
FIG. 4, L4 lumbar vertebra: axial view transverse process transected.
Figure 10A:
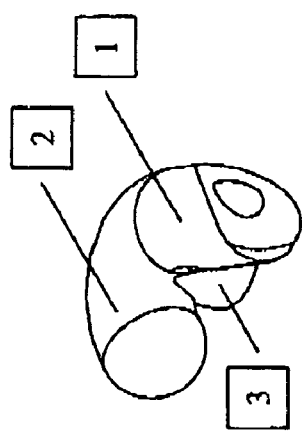
FIG. 10, 4 views: three bone cuts/expansions.
Figure 10B:
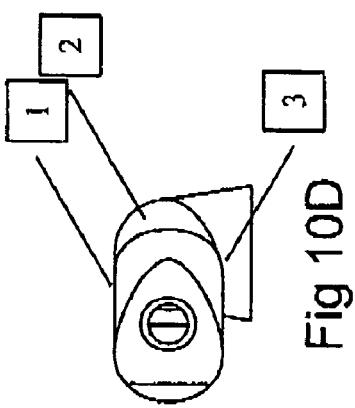
Figure 10C:
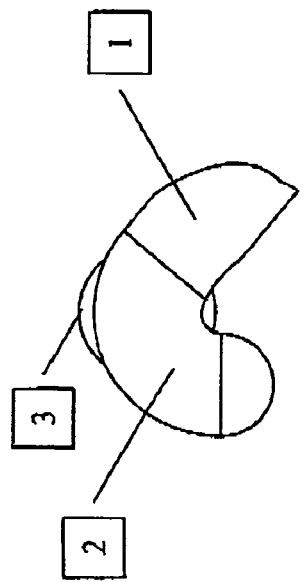
Figure 10D:
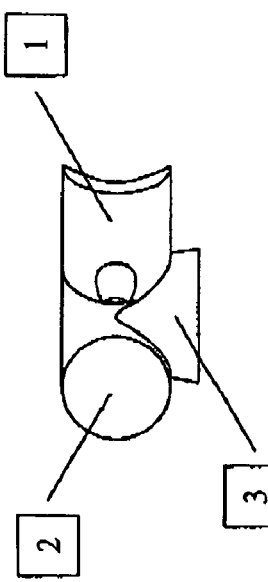

FIG. 4 shows a division of the right transverse process at L4 (shown at the cross-sectioned area 8). The division of the transverse process improves the surgical exposure facilitating visualization and guide pin placement, etc., preferably at an angle as shown in FIGS. 5A-C and discussed below. The transverse process can be reattached at the end of the case if desired. Further dissection after transaction of the transverse process follows the lateral wall of the L4 body. Hemostasis is achieved by cautery, etc.

FIGS. 5A, B and C demonstrate a preferred positioning of the guide pin for a specific posterior lateral approach. The guide pin is placed at an angle of substantially 50° (40°-75°) from a point directly above and centered on the footprint of the nucleus pulposa of L4-5 and on a line centered in the L4 body connecting the center of the L4 body and spinous process. This angle is for the specific posterior-lateral approach described. A first vertebral body can be entered at any angle preferred by the surgeon. L5 can be entered first and the cuts and the implants placed in the cephalad direction instead of the caudad direction describe here, which starts at L4 in the direction of L5.

The guide pin is preferably positioned and centered in anterior/posterior, medial lateral and axial planes. It is preferably placed parallel to the endplates of L4. It is small in diameter, drilled into places precisely. The surgeon may elect to vary the position of the guide pin as necessary for each particular case. Also other approaches and combinations of approaches will require variations of guide pin placement. Placement of the pin is verified in more than one plane by x-rays, ultrasound (US), computer navigation, etc.

FIGS. 6A, B and C show the TOSCA core being cut. The TOSCA core cutter is typically cannulated and fits over a guide pin. The depth of the core cut is calibrated from preoperative tests. The TOSCA core cutter is set for the appropriate cut depth. The cut is checked in more than one plane and several times as the core cut is being made. The TOSCA core cutter is a specially designed annular cutter and will be discussed in detail later (see FIG. 16 below). (1 is the guide pin, 2 is the core cut outline, 3 is the L4 body and 4 is the spinal canal.)

FIGS. 7A and B show the TOSCA core being removed. Before it can be removed the core has to be transected at its base. Several different TOSCA core transectors will be shown and discussed later (see FIGS. 13-15). The bone core is removed and then is saved for later use. Replacement of the bone core at the end of the surgery will immediately fills the stress riser made by the core cut and removal of the core and the bone fracture (i.e. bone core/bone core hole) then heals and obliterates the stress riser. (1 is the guide pin, 2 is the core cut outline, 3 is the L4 body, 4 is the spinal canal and 7 is the bone core.)

FIGS. 8A, B, C and D show different views of the TOSCA core. This figure shows a core that was divided diametrically perpendicular to its long axis to accommodate a particular core transector, (see FIG. 14 below). (1 is the bone core, 2 is the plane of the division into halves, 3 is the guide pin hole.)

FIGS. 9A, B and C show two additional cuts made and/or bone removed from the L4 body to accommodate the implants as well as to improve access the L4-5 disc space and the L5 vertebral body (2 is the core hole, 3 is the L4 body, 4 is the axial cut and 8 is the core hole extension).

FIGS. 10 A, B, C and D show different views of the three bone cuts/extensions (assembled volumes of the three portions of bone removed). (1 is the bone core cut, 2 is the bone core extension and 3 is the axial cut through the lower body endplate of L4.)

FIGS. 11A, B and C show the positioning of the axial cutter in L4. (3 is L4, 4 is L5, 6 is the L4-5 disc and 9 is the axial cutter in position.)

FIGS. 12 A, B, C and D show the axial cut through L4 and the cut for the crown and post fixation (patent pending) in L5. This is a specific cut for a particular implant fixation method made by a specially designed cutter, (see FIG. 21 below). The cut in general can be made by any type of cutter, burr or drill. The progression of the cut should be checked multiple times in more than one plane and by more than one method. (1 is L4, 2 is the core hole, 3 is the post cut in L5 (see FIG. 21 below for more detail), 4 is L5 and 5 is the L4-5 disc.

FIGS. 13 A, B, C and D shows one embodiment of a TOSCA core transector (TCT). Cutting blades (3) rest on the sides of the shaft (1) to allow insertion of the TCT into the guide pin hole. Once the tip of the TCT (4) reaches the appropriate depth in the guide pin hole the shaft is connected to a drilling mechanism. As the shaft and blade is rotated it is deployed by pushing on the sleeve (2) which deploys the blades as they cut. The blades can be cycled through open-closed states as the cutting is in progress. This TOSCA core transector cuts a cone shaped void out of the end of the bone core in a direction away from starting position with the blades of the TCT not deployed, which then intersects with the TOSCA core cut, allowing the core to be removed. The blades can be made of any appropriate material, preferably a metal. They can be made of NiTi nickel-titanium alloy (Nitinol) or any other memory or smart material. (1 is the shaft, 2 is the cutter sleeve, 3 are the cutting blades [fully deployed] and 4 is the terminal end of the cutter shaft.)

FIGS. 14A, B, C and D shows another embodiment of the core transector. This device requires that the core is additionally divided in half on a line 90° to the long axis of the TOSCA bone core. This core transector fits into the guide pin hole, the TOSCA core cut and the diametrically divided bone core. It is inserted until it reaches the proper position and then turned in a substantially oscillating fashion to transect the core. The cutting elements or core transector can be made of any appropriate material, preferably a metal. It can be made of NiTi or any other memory or smart material. (1 is the shaft, 2 is the cutting blade and 3 is the ring that fits into the core cut).

FIGS. 15 A, B, C and D demonstrates another embodiment for the core transector. The flexible cutting elements wind tightly to the shaft. They are tipped with box shaped cutters. The device is inserted with the cutting elements wound tight to the shaft and held in place by a sleeve (not shown). Once the device is in position the shaft is connected to a drilling mechanism. The sleeve is withdrawn partially and the spinning motion of the shaft driven by the drill mechanism helps deploy the cutting elements. After the core is transected the sleeve is used to secure the cutting elements and it is removed with the core. The cutting elements or core transector can be made of any appropriate material, preferably a metal. It can be made of NiTi or any other memory or smart material. The core transector can be provided with thermal, RF, laser cutting element(s) or any other practical energy source to make the bone cuts (1 is the shaft and 2 is one of the cutting elements).

FIGS. 16A, B, C and D demonstrate a specialized annular cutter for the initial TOSCA core cut. There is a cannulated central drill bit held to the annular cutter body by a Morris taper. The annular cutter is shown with flutes on the outside of the body. Flutes can be on the inside as well [see below in more detail and FIG. 29]. The wall thickness of the annular cutter can be as thin as (0.005") when used in a specialized cutting assembly (patent pending). (1 is the shaft, 2 is the drill cannulation, 3 is the inner drill and 4 is the wall of the annular cutter.)

FIGS. 17A, B and C show an embodiment of an axial cutter. It can be used to cut through the body of L4 to the L4-5 disc space and/or into L5 body. A recessed telescopic cutter/funnel (TCF) assembly is housed in the axial cutter assembly. The TCF is deployed after the axial cutter is properly positioned. The telescopic elements, when deployed, form a funnel to collect bone cutting debris. Water can be introduced into the cutting site from one or more apertures in the cutting blade. Suction can be applied to the end of the funnel to aid in the collection of the bone cutting debris. (1 is the housing of the axial cutter and 2 is the cutter/driver.)

FIGS. 18A, B, C, D and E show another embodiment of an axial cutter. This embodiment has an array of ultrasound (US) sensors. Part of the US array is disposed radially. Part of the US array is disposed axially. The US sensors can be of any type and incorporated in any fashion or disposed in any fashion into or on the housing of the axial cutter. The US gives real-time position and orientation independent of other methods of evaluating the position of the device. US can be used in any of the other instruments to help guide them interoperatively. (1 is the axial cutter housing, 2 is the cutter/driver and 3 is the US array)

Figure 19D:
FIG. 19, 4 views: axial cutter cutting mechanism (embodiment 1) closed.
Figure 19B:
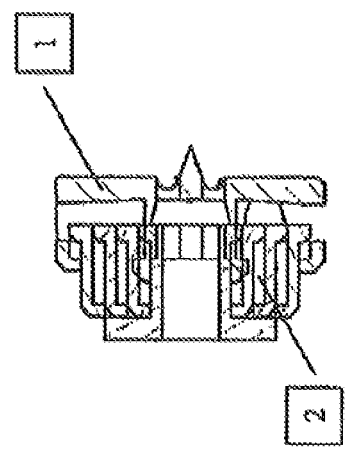
Figure 19C:
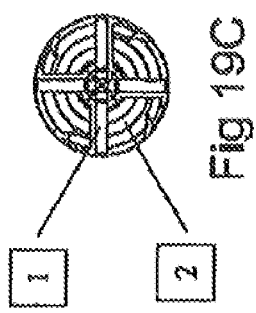
Figure 19A:
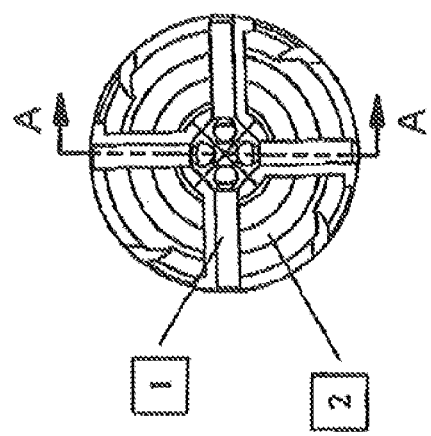

FIGS. 19A, B, C and D show a detail of the TCF. This embodiment shows a cutting element with four blades. There are four telescoping units that form a funnel when deployed. There are four ports at the center of the cutting blade to allow for suction and irrigation. The TCF is closed in these figures. This closed position allows the TCF to be recessed in the axial cutter housing for placement. The TCF is then gradually deployed (see FIG. 20 below).

FIGS. 20A, B, C and D show a detail of the TCF. This embodiment shows a cutting element with four blades. There are four telescoping units that make a funnel when deployed. There are four ports at the center to allow for suction and irrigation. The TCF is fully deployed in these figures. This deployed position allows the TCF to be cut the axial hole in L4 for access to the l4-5 disc space and L5. The cut can be continued into L5. The TCF is gradually deployed as the cutting takes place. It is then retracted after the cuts are made and removed.

FIGS. 21A, B, C, D and E show the cutting element for the crown and post fixation. The cutting element is another annular type cutter used for the crown and post fixation. There is typically a central cannulated elongation that can also be fashioned as a drill bit. There can be flutes on the inside and/or outside of the crown and post fixation cutter element. The flutes can be any size and any number. The pitch of the flutes can be any practical pitch to remove bone cutting debris. The flutes can have cutting edges like a drill bit. The pitch can vary on a single surface (i.e. outside). The pitch can be different on the inside and outside surfaces of the annular cutter. There is a single tooth in this embodiment. Any number of teeth and any practical tooth size can be used. The shape of the tooth can be designed to cut different size flakes and also be matched to the flute size for efficient removal of cutting debris. (1 is the shaft, 2 is the cannulation in the shaft, 3 is the outside flute cutter, 4 is the inside flute cutter, 5 is the elongation/drill, 6 is one of the hole for egress of debris and 7 is the cutting tooth.)

FIGS. 22A, B, C, D and E show a basic embodiment of a series of embodiments of a spinal disc/nucleus replacement (SDNR). The SDNR can be one or more parts. It can be a single unit at least partially made of a flexible material that can tolerate and withstand the forces, torques and motions of the spine. The SNDR can be modular. The modular elements can be for specific functions of fixation to the bone, structural integrity and articulation, etc. The modular elements can also designed to facilitate implantation. Any of the modular elements can have accessory features or parts. This first embodiment (E1) shows a SDNR with 3 parts. The first part which the L5 component (1) is inserted into L5 after L5 is prepared. This E1 shows a threaded type of fixation for both L4 and L5. The threaded fixation is used to indicate any practical type of fixation. The fixation can be flutes, spines, elongations, fins, steps, frames and projections. It can also be threads, channels, grooves, keyways etc. The L4 and L5 implants can be cemented with PMMA or any other adhesive. The adhesive can harden to any solid physical state. It can be substantially rigid like PMMA or substantially flexible like silicone. The fixation parts of the implants can allow bone in growth. They can be coated with a porous surface and the like to encourage and allow bone in growth by any method known in the art. They can be coated with hydroxyapatite or bone morphogenic protein (BMP) or like material, promotes bone in growth. The material can be bioactive. The components can be fenestrated to allow bone graft to be placed in and/or on the fixation portion. The L4 and L5 implants can be made of any appropriate material, preferably a metal. It can be made of NiTi or any other memory or smart material. It can be a plastic, a ceramic, a carbon-based material or any other biocompatible material.

The bodies of the L4 (3) and L5 (1) components can have an articulation surface [AS]. The AS can match the contour of an AE (2) or there can be a difference in the shape and contact surfaces of the AS and the AE. The shape of the AS can be different in the L4 and L5 components. The AS can additionally have one or many recesses or wells to provide areas where there is no contact with the AE. This embodiment shows a single recess or well at the point of maximal axial contact. The AE (2) with an AS with a central recess or well will then rest on a ring or larger surface area than a point when the surfaces of the AS and the AE are not congruent.

The well can also be used to trap wear debris (patent pending). The trap can also be filled with a material that accepts and sequesters the wear debris as it is forced into the material during motion or load such as PTFE (teflon). PTFE is softer than UHMWPE and also acts as a coating to the surface that glides over the PTFE in the well. The PTFE is displaced up and out of the well as the volume of the well is filled with wear debris of any type. Any other suitable material can be used to be used in the well to trap the UHMWPE and/or metal, etc., wear debris. Magnetic material can be used in a well to trap metal ions from metal-metal articulations especially, Fe, Co, Ni and Cr and the like that can be influenced by magnetic fields.

The AE is placed through the bone core hole after the L5 component is fixed to the bone. The AE (2) in this embodiment is substantially ellipsoid or discoid. It can be made of any biocompatible material that can accept the stresses applied. It can have symmetric or asymmetric surfaces such as upper and lower. It can be made of a substantially hard material such as metal, ceramic, plastic, carbon based material and the like. It can be made of a viscoelastic material, an elastic material or any other biocompatible or biologic material with desired physical properties (i.e. a hydrogel). The AE can be solid or have one or more voids. The voids can be filled with other materials such as solids, liquids or gases. The AE can be made of any appropriate material, preferably a metal. It can be made of NiTi or any other memory or smart material. It can be a plastic, a ceramic, a carbon-based material or any other biocompatible material. The size of the AE is dependent on the amount of flexion desired. Larger dimension in the axial direction allows more flexion by greater separation of the components. The shape can be such that it controls or limits any motion in six degrees of motion by its interaction with the contour of the articulating surface of L4 and L5. (i.e. anterior/posterior, medial/lateral, radial tilt, etc.). The AE can be placed in any appropriate position between/on or in the other components. There can be one or more than one AE disposed at the interface. The multiple AE elements can be different size, shape and/or material. The embodiments with more than one AE can have the AEs distributed in any fashion or pattern.

The L4 component is placed through the bone core hole to engage the AE After assembly the L4 component is adjusted to the proper depth and pressure with a torque driver or the like. Flexion of the spine at the treated level is tested before closure.

FIGS. 23A, B, C, D and E show another SDNR embodiment. This embodiment has L4 and L5 flanges that can be put through the L4 core hole in a modular fashion. The L5 flange is placed first as one or (two or more units and assembled) before the L5 component. The L5 component engages the flange(s) and locks it in place. The flange stabilizes the L5 implant. The L5 flange can be made of flexible material to allow it to be inserted as a single unit. It can likewise be a material that is inserted as a liquid or in a soften state and then hardens. It can be modular. It can be made of a metal, ceramic, plastic, carbon based material and the like. The flange(s) can be made of a metal with a memory such as a nickel-titanium alloy (Nitinol) or any other memory metal or smart metal. It can also be hard, viscoelastic, elastic, etc. It can be made and shaped out of a spring steel or the like or any other material that retains the ability it absorb energy or impact. The size and shape can be any appropriate size and shape. After the AE is placed the L4 flange parts are placed and secured with the L4 component. Otherwise this embodiment incorporates substantially all the elements of FIG. 22.

FIGS. 24A, B, C, D and E show a combination of many features available to the SDNR designs. Each element or modular part has additional features from the previously demonstrated embodiments. FIG. 24 shows one of many combinations of features. Fixation can have protrusions, elongations, grooves, flutes and the like. Fixation can be static, expandable or deployable, either mechanically or thermally by a method such as a memory metal. Fixation elements can have additional screws, pins and the like. FE can be fenestrated. The FE can be modular. The fixation element can be separate from the AS.

Specifically FIG. 24 shows a L5 component (1) (see detail of FIG. 26) that utilizes the crown and post fixation. There are two anti-rotational elements on the body of the component. The L5 component has an axial guide/support. The L5 component is fenestrated. The L5 implant can be made of any appropriate material, preferably a metal. It can be made of NiTi or any other memory or smart material. It can be a plastic, a ceramic, a carbon-based material or any other biocompatible material. The L5 component has two fixation screws (2, 3). The L5 articulating surface (4) attaches to the L5 FE by Morris taper and anti-rotational elongations in the AS. The AS of the L4 and L5 has a well or wells to collect wear debris and increase the contact area with the AE. The AS contour is not a line fit with the AE. The AE in this embodiment has an offset surface (OS) (patent pending). An OS has a larger surface radius (R1) than the center of rotation (R2). The R1 of the AE substantially matches at least a portion the R1 of the AS. This allows less constraint and greater contact area.

The L4 and L5 AS can additionally have an array of magnetic material (Hyde, U.S. Pat. No. 6,387,096) disposed in the flanges that interact substantially in repulsion, attraction or both. The magnetic arrays provide a dynamic interface to absorb energy in flexion and axial loads. The magnetic arrays also can provide stability. The AE can be magnetized independently or indirectly by contact with a magnetic material.

The articulating surface (6) of this L4 implant has an elongation (7) that keys into the body of L4 (8). The elongation (7) can be modular from the articulating surface (6). There are two fixation screws (9, 10). One (9) interlocks 7 with 8 and fixes the L4 body to the bone. Screw (10) fixes the body (8) to the bone.

FIGS. 25A, B, C, D and E show the embodiment in FIG. 24 implanted in L4 and L5.

It is understood by those familiar with the art that a more complicated implant requires more steps and presents greater difficulty for the surgeon and requires more time for implantation. Likewise it is understood that the fixation, stability, structural integrity, articulation motion and durability are important. Design elements will be chosen for particular embodiments that balance these factors depending on the demand and spinal level (i.e. cervical, thoracic and lumbar).

FIGS. 26A, B, C, D and E show details of the L5 crown and post fixation. FIG. 26A is the AP view. (1 is the body of the L5 component, 2 is the axial elongation, 3 is one of the anti-rotational elongations, 4 is the Morris taper, 5 is the anti-rotational elongation, 6 is one of the holes for the fixation screws and 7 is one of the fenestrations.)

FIGS. 27A and B show the L5 crown and post fixation element implanted in L5 (1). (1 is L5, 2 is L4, 3 is the L4-5 disc, 4 is nucleus pulposa footprint and 5 is the L5 crown and post fixation element.)

FIGS. 28A, B, C, D and E show 5 views of a different L5 crown and post fixation element.

FIGS. 29A, B and C show the FIG. 28 L5 crown and post fixation element implanted.

FIGS. 30A, B, C, D and E show an accessory fixation device to the L5 component from FIGS. 22 and 23. The accessory fixation deploys as the L5 component is screwed into place. (1 is the L5 component and 2 is one of the elements that deploys.)

The methods for treating spinal pathology according to the invention include not only artificial disc implants but also nucleus pulposa implant, fusion with a special implant, tumor treatment, vertebralplasty and other procedures in which the treatment region is advantageously reached by the described transosseous core approach.

It is to be understood that, while various embodiments of the invention have been described in conjunction with the detailed description thereof, the foregoing is intended only to illustrate and not to limit the scope of the present invention, which is defined by the scope of the specification and by future claims. Other equivalent embodiments, aspects, advantages, and modifications are within the scope of the specification and claims to be made.

I claim:

1. A transosseous method for treating the spine, comprising:
    making an incision through tissue to expose one or more vertebrae,
    positioning a guide pin laterally in the vertebral body spaced from posterior features of a vertebra containing at least in part a site of interest for intervention;
    advancing a rounded cutting instrument over the guide pin directly into the vertebral body of the vertebra containing the site of interest, the cutting instrument having a diameter extending substantially between the end plates of said vertebra;
    cutting a bone aperture, the aperture having a rounded opening with a dimension extending substantially between the vertebral end plates into the bone of a single vertebra to serve as an access window, and removing bone material, to reach the site of interest through the bone aperture,
    performing an intervention at the site of interest, and
    reimplementing at least a portion of the bone material in the rounded opening.

2. The method of claim 1, wherein the bone aperture is made in a vertebra in the lumbar region of the spine.

3. The method of claim 2, wherein the bone aperture is approximately 0.8" in diameter.

4. The method of claim 1, wherein the incision is made and the bone aperture is cut from a generally posterior side of the patient.

5. The method of claim 1, further including, following provision of the bone hole aperture, introducing a second cutter into the vertebra through the bone aperture, and, using the second cutter, making a second cut in the vertebra substantially along a different axis relative to the axis of the bone aperture.

6. The method of claim 5, wherein the different axis is generally perpendicular to the axis of the bone aperture and generally axial to the spine.

7. The method of claim 5, further including continuing the second cut into the disc space between two vertebrae.

8. The method of claim 7, further including removing loose material produced by the culling.

9. The method of claim 8, wherein the step of removing loose material includes removal of at least part of a disc between the vertebrae.

10. The method of claim 1, wherein the step of cutting a bone aperture comprises cutting into the vertebra at an angle of about 40° to 70° to the patient's sagittal plane.

11. The method of claim 1, wherein the cuffing of the bone aperture is made with an instrument capable of cutting a bone core and wherein the step of removing the bone material includes removing a bone core.

12. The method of claim 1, wherein the cutting of the bone hole is made with an instrument capable of cutting a bone core and wherein the step of removing the bone material includes removing a bone core.

13. The method of claim 1, wherein the intervention comprises implanting a spine prosthesis, and including attaching the spine prosthesis to the vertebrae in which the bone aperture is formed.

14. The method of claim 13, wherein the spine prosthesis is substantially modular and includes at least two components, and the method includes fixing at least one of the components to the bone of at least one of two adjacent vertebrae, and including retaining the articular element between the two components.

15. The method of claim 14, wherein the step of fixing the components comprises cementing the components to at least one of the two adjacent vertebrae.

16. The method of claim 14, wherein the at least one of the components has bumps, flutes, spines or elongations for engaging against sides of a bone hole, and the step of fixing includes engaging the bumps, flutes, spines or elongations tightly against or into the bone at the bone hole.

17. The method of claim 14, wherein the fixing step includes fastening at least one of the components to the bone by engaging screws, pins or rods between a component and a vertebral bone.

18. The method of claim 14, wherein at least one of the components is secured to at least one of the vertebrae by press fit.

19. The method of claim 13, wherein the spine prosthesis is a fusion device, a partial disc replacement, a disc replacement or includes an articular surface.

20. The method of claim 13, wherein the spine prosthesis is substantially modular and includes at least two components and the method includes fixing at least one component to the bone of at least one of two adjacent vertebrae.

21. The method of claim 20, wherein at least one of the components has screw threads which are screwed into the bone of at least one of the adjacent vertebrae.

22. The method of claim 20, wherein the method includes connecting two of the components.

23. The method of claim 20, wherein the spine prosthesis is substantially modular and includes at least two components and the method includes connecting two of the components by at least one connector component.

24. The method of claim 20, wherein the components have surface textures for engaging the bone of a vertebral body, and the step of fixing includes engaging the surface textures against the bone.

25. The method of claim 20, wherein the components have surface elements for engaging the bone of a vertebral body, and the step of fixing includes engaging the surface elements tightly against or into the bone.

26. The method of claim 20, wherein the fixing step includes fastening at least one of the components to the bone.

27. The transosseous core method of claim 20, wherein at least one of the components is secured to at least one of the vertebrae by a crown-post fixation technique.

28. The method of claim 1, wherein positioning the guide pin comprises orienting the guide pin along an axis extending through the center of the vertebral body in a transverse plane at an angle of 40-75 degrees from a line through the center of the vertebral body and the spinous process.

29. A transosseous method for implanting a spinal prosthesis, comprising:
    forming a first aperture through a vertebra in the vertebral body spaced from posterior features, at an oblique angle to the sagittal plane of the patient, and including cutting substantially to the center of the vertebral body,
    removing material from the vertebral body to provide the first bone aperture,
    forming a second hole generally along a different axis to the orientation of the bone aperture, and including cutting through the endplate of at least one vertebra into a space of nucleus pulposa between two adjacent vertebrae,
    removing loose material left after the cutting, inserting an implant through the first bone aperture and then into a substantially axial orientation and fixing the implant to two adjacent vertebrae, substantially in the second hole formed with the second cutter, and closing the first bone aperture.

30. The method of claim 29, wherein said first aperture is formed by entering the vertebra through the vertebral body between the endplates.

31. The method of claim 29, wherein the first aperture is formed along a first axis and said different axis is a second axis.

32. The method of claim 31, wherein the first aperture along the first axis directly intersects the second hole along the second axis.

33. The method of claim 32, wherein the said cuffing into the space of the nucleus pulposa comprises cutting into the nucleus pulposa of the L4-5 disc space.

34. The method of claim 29, wherein closing the first bone aperture comprises replacing material removed to provide the first aperture.

35. The method of claim 34, wherein forming the first aperture comprises removing a bone core and closing the first aperture comprises replacing the bone core.

36. The method of claim 29, wherein positioning the guide pin comprises orienting the guide pin along an axis extending through the center of the vertebral body in a transverse plane at an angle of 40-75 degrees from a line through the center of the vertebral body and the spinous process.

* * * * *